(12) United States Patent
Saito et al.

(10) Patent No.: US 7,883,865 B2
(45) Date of Patent: Feb. 8, 2011

(54) PRODUCTION OF CELL CULTURE PRODUCT AND MATERIAL FOR USE IN SAID PRODUCTION

(75) Inventors: Nagahiro Saito, Nagoya (JP); Osamu Takai, Nagoya (JP); Yunying Wu, Nagoya (JP); Hiroyuki Honda, Nagoya (JP); Akira Ito, Nagoya (JP)

(73) Assignee: National University Corporation Nagoya University, Aichi (JP)

( * ) Notice: Subject to any disclaimer, the term of this patent is extended or adjusted under 35 U.S.C. 154(b) by 565 days.

(21) Appl. No.: 11/574,949

(22) PCT Filed: Sep. 8, 2005

(86) PCT No.: PCT/JP2005/016989

§ 371 (c)(1),
(2), (4) Date: Sep. 20, 2007

(87) PCT Pub. No.: WO2006/028274

PCT Pub. Date: Mar. 16, 2006

(65) Prior Publication Data

US 2008/0032403 A1    Feb. 7, 2008

(30) Foreign Application Priority Data

Sep. 8, 2004    (JP) .............................. 2004-261216

(51) Int. Cl.
C12P 21/02    (2006.01)
(52) U.S. Cl. ..................................... 435/69.1; 435/402
(58) Field of Classification Search ........................ None
See application file for complete search history.

(56) References Cited

U.S. PATENT DOCUMENTS

2002/0095219 A1    7/2002    Nelles et al.
2002/0182241 A1    12/2002    Borenstein et al.
2004/0018615 A1    1/2004    Garyantes
2004/0235167 A1    11/2004    Miyake et al.
2005/0186674 A1    8/2005    Miyake et al.
2005/0208656 A1    9/2005    Miyake et al.

FOREIGN PATENT DOCUMENTS

| JP | 57-146568 | 9/1982 |
|---|---|---|
| JP | 02-84174 | 3/1990 |
| JP | 03-7576 | 1/1991 |
| JP | 05-192138 | 8/1993 |
| JP | 06-335381 | 12/1994 |
| JP | 2000-087016 | 3/2000 |
| JP | 2002-502955 | 1/2002 |
| JP | 2002-283530 | 10/2002 |
| JP | 2002-355031 | 12/2002 |
| JP | 2003-527615 | 9/2003 |
| JP | 2004-98351 | 4/2004 |
| JP | 2004-105043 | 4/2004 |
| JP | 2004-344025 | 12/2004 |
| JP | 2005-143382 | 6/2005 |
| JP | 2005-160441 | 6/2005 |
| WO | 01/70389 | 9/2001 |

OTHER PUBLICATIONS

International Search Report for PCT/JP2005/016989 dated Dec. 27, 2005.
International Preliminary Examination Report for PCT/JP2005/016989 dated Jan. 12, 2007.

*Primary Examiner*—James S Ketter
(74) *Attorney, Agent, or Firm*—Turocy & Watson, LLP

(57) ABSTRACT

A base plate for use in cell culture which comprises a base material, a water-repellent layer having a water-repellent surface formed on the above base material and a hydrophilic surface having a prescribed pattern formed on the base material; a method for producing the above base plate; and a method for producing a cell culture product using the base plate. It is preferred that the water-repellent surface has a water contact angle of more than 150°. The above method for producing a cell culture product using the base plate base plate is a novel method which allows the production of a cell culture product of a fine pattern.

15 Claims, 20 Drawing Sheets

A   B

PRODUCTION OF CELL CULTURE
PRODUCT AND MATERIAL FOR USE IN
SAID PRODUCTION

TECHNICAL FIELD

The present invention relates to a method for producing a cell culture product in a desired pattern, a cell culture plate that can be favorably used in said method, and a method for manufacturing said plate. More specifically, the present invention relates to a method capable of producing a cell culture product along a fine pattern formed of a water-repellent surface and a hydrophilic surface, a cell culture plate that can be used in said production, and a method for manufacturing said plate.

BACKGROUND ART

Due to the development in culture technique of cells and tissue, analyzing (diagnosing), from various viewpoints, cultured-cells or the like extracted from various specimen has become readily accessible. Further, the progress in tissue engineering has accelerated the development of regenerative medical technique for regenerating parts of a body that are actually lost, and regenerative medical practice utilizing such technique for clinical application has also become common and has been already applied to regenerated skin and the like.

However, further development in regenerative medical practice or diagnosis at the cell (or tissue) level requires production of a cell culture product (including cultured tissue, and hereinafter alike) of a desired form, structure and pattern (hereinafter collectively refers to as a "pattern"). In recent years, in order to culture cells to a state closer to living organism, attempts have been made to form a shape and structure that are the same as living organism.

For example, Japanese Patent Publications H2-84174, H6-335381 and 2002-355031; and Japanese Translation No. 2003-527615 of PCT International Application (WO01/070389) disclose cell culture plates, on which a pattern is formed with a functional group, polymer membrane, cell-growth promoting molecule or cell adhesion promoting agent; to which cells readily adhere, and methods for forming the cell pattern. In addition, Japanese Patent Publication 2004-105043 discloses a technique for patterning a hydrophilic region on a cell culture plate, applying a non-cell-adhesive treatment to the regions other than the patterned region on the plate, and selectively forming a cell pattern in the pattern region.

DISCLOSURE OF INVENTION

Several tissues and organs (for example, capillary vessels) within a living organism have an extremely intricate form or structure. Therefore, in order to perform histochemical analysis or apply regenerative medical technology on such intricate tissue or organ, a production technology for cell culture products having finer and more diverse patterns than the conventional ones has been anticipated. For example, if a patterned capillary network or nerve tissue network can be formed/produced in accordance with the patient, this will greatly contribute to the progress of regenerative medical practice.

The present invention has been developed to achieve the following objects. One of the objects of the present invention is to provide a new method capable of producing a cell culture product having a fine pattern (including a culture product (living tissue) assuming the shape of a prescribed pattern). Another object is to provide a cell culture plate that can be favorably used in such production method and a method for fabricating such plate. In addition, another object of the present invention is to provide a cell culture product in a desired fine pattern (for example, a culture product organized and formed into a tubular shape such as a blood vessel) produced by the method described herein.

In order to achieve the above-described objects, the present invention provides a cell culture plate including a substrate, a water-repellent layer having a water-repellent surface formed on the substrate, and a hydrophilic surface having a prescribed pattern formed on the substrate.

The present invention also provides a method for manufacturing such a cell culture plate (in other words, a plate for production of cell culture product). The method for manufacturing a cell culture plate described herein includes preparing an appropriate substrate, forming a water-repellent layer having a water-repellent surface on the substrate, and forming a hydrophilic surface having a prescribed pattern on the substrate.

In one of the typical manufacturing methods, an appropriate substrate is prepared and a water-repellent layer having a water-repellent surface is formed on the substrate. Thereafter, a portion corresponding to a prescribed pattern is removed from such water-repellent surface, and a hydrophilic surface having the prescribed pattern is formed in such portion.

Note that in the present specification, "plate" or "substrate" generally refers to a support material for culturing cells in a prescribed pattern (therefore, a substrate having a cell culture bed), and is not limited to a specific shape or structure. For example, the plate (substrate) may be planar, curved, or in a desired three-dimensional shape.

The term "removed" related to the above water-repellent surface includes removal of a part of the water-repellent layer constituting the portion of the water-repellent surface corresponding to the prescribed pattern, and also modification and destruction of the water-repellent layer (water-repellent surface) at the molecular level.

The removal (including modification and destruction) of the portion corresponding to the prescribed pattern is preferably performed by lithography. In the present specification, "lithography" refers to a microfabrication technology forming a desired fine pattern on a processing material by irradiating light or other electromagnetic energy; ion beam or other converging heat energy; or the like on the processing material in a prescribed pattern. Formation of a circuit pattern on wafer (photolithography) performed with an appropriate photo mask and exposure equipment in fabrication of semiconductor devices is a typical example of such lithography. By applying such lithography, microfabrication can be performed on a part of the water-repellent surface, and a hydrophilic surface (therefore, a cell culture surface) in an extremely fine pattern can be accurately produced on a part of the water-repellent layer (therefore, the non-cell-culture surface). Further, since the prescribed hydrophilic pattern is directly formed on the substrate serving as the cell culture bed, errors and deviations in the pattern position are prevented, and a fine prescribed pattern can be reproduced with accuracy.

Alternatively, removal of the portion corresponding to the above prescribed pattern can also be favorably performed by abrasion using various lasers.

In another one of the typical methods for manufacturing a cell culture plate, a substrate having a hydrophilic surface (for example, a substrate of which surface is coated with a hydrophilic substance such as gelatin or collagen) is prepared, and a water-repellent layer having a water-repellent surface is formed surrounding and leaving a portion of the hydrophilic surface having a prescribed pattern on the substrate. Preferably, the formation of the water-repellent layer surrounding and leaving the portion of the hydrophilic surface having the prescribed pattern is performed by lithography.

On a cell culture plate provided by the present invention, culture medium may be selectively disposed on the hydrophilic surface having a prescribed pattern, and target cells can be adhered. The portion around the pattern is constituted with a water-repellent layer having a water-repellent surface. Therefore, for example, when a small quantity of culture medium is supplied to a cell culture plate provided by the present invention, the culture medium (culture solution) will be repelled from the water-repellent surface. In this case, culturing cells on the water-repellent surface is virtually impossible.

In the cell culture plate described herein, the boundary of the prescribed pattern is clearly defined, and on the hydrophilic surface of a prescribed pattern (preferably a fine pattern formed by applying lithography on the water-repellent layer), culture medium can be selectively disposed having a well-defined boundary and a cell culture product (including a cell aggregate and an organized culture product) formed according to such pattern can be obtained. Further, since the aqueous medium (culture solution) disposed on the hydrophilic surface of the fine pattern is prevented from effusing to the water-repellent surface, typically, the culture medium can be kept as protruding droplets. As a result, when a cell culture plate provided by the present invention is used, although it also depends on the kind and nature of the cells to be inoculated, can be obtained a three-dimensional cell culture product grown not only planarly, but also heightwise (for example, a minute tissue or organ shape). Note that a "cell culture product" in the present specification refers to a group of cells (for example, a cell aggregate or tissue) cultured in a culture medium of a prescribed composition and form, and is not limited to specific characteristics.

Another aspect of the present invention provides a method for producing a cell culture product in a desired pattern, the method comprising preparing a plate for culturing cells, the plate having a hydrophilic surface formed in a prescribed pattern and a water-repellent surface formed in areas other than the pattern; selectively disposing culture medium on the hydrophilic surface; and culturing target cells (for example, stem cells such as ES cells, and other floating cells) in the disposed culture medium. Typically, the method for producing a cell culture product in the present embodiment can be favorably carried out by using any of the cell culture plates described herein.

According to the method of such a scheme, culture medium is selectively disposed on the hydrophilic surface of a prescribed pattern on the plate. At this time, since the portion around the pattern on the plate is a water-repellent surface, the culture medium (typically, culture solution) will be repelled and not retained by such surface. As a result, even if the culture medium is not precisely disposed according to the pattern, the culture medium can be readily placed along the pattern, developing a clear boundary. The culture medium can be kept preferably as protruding droplets. Therefore, according to the present production method, can be produced a cell culture product organized in a prescribed pattern on the base plate. Alternatively, a cell culture product (can be a tissue fragment) having a two-dimensional or three-dimensional shape formed in a fine and precise pattern can be produced in the culture medium disposed along the pattern.

Alternatively, according to a cell culture plate described herein, even when excess culture medium is supplied (when even the water-repellent surface is filled with culture medium), cells are unlikely to adhere (attach) to the water-repellent surface, and various types of adherent cells (for example, vascular endothelium cells, neural cells, fibroblasts) are adhered only to the hydrophilic surface in the prescribed pattern, and can be cultured and produced as a culture product (a cell aggregate or tissue) formed in the pattern corresponding to the pattern of the hydrophilic surface.

Therefore, another aspect of the present invention provides a method for producing a cell culture product of a desired pattern, the method comprising preparing a plate for culturing cells, the plate having a hydrophilic surface formed in a prescribed pattern and a water-repellent surface formed in areas other than the pattern; and culturing adherent cells of interest in a state where the cells are selectively adhered onto the hydrophilic surface. Typically, the method for producing a cell culture product in the present embodiment can be favorably performed by using any of the cell culture plates described herein.

According to the method of such a scheme, as a result of using a plate having the above-described structural features, adherent cells may be selectively adhered to the hydrophilic surface in a prescribed pattern on the plate. Further, since the portion around the pattern on the plate is a water-repellent surface, cell attachment is inhibited on such surface. As a result, without requiring any specific operation, the target cells can be precisely deposited on the hydrophilic surface in accordance with the pattern. Therefore, according to the present production method, can be formed/produced a cell culture product composed of adherent cells deposited in a prescribed pattern on the plate. Furthermore, can be produced a cell culture product (for example, string-shaped or tubular tissue such as capillary vessels extending in a designated pattern) having a two-dimensional or three-dimensional shape formed in a fine and precise pattern.

In a preferred embodiment of a cell culture plate provided by the present invention, the water-repellent layer is a monomolecular layer. In a preferred embodiment of the method for manufacturing a cell culture plate described herein, the water-repellent layer is formed as a monomolecular layer.

Since the water-repellent layer is a monomolecular layer constituted with a prescribed compound, the water-repellent layer can be a thin layer of an approximately uniform thickness. In addition, a monomolecular layer allows the repellency of the water-repellent surface to be more uniform. Further, it allows the irregularities on the water-repellent surface and the hydrophilic surface to be approximately uniform, and culture medium can be approximately evenly disposed across the entire hydrophilic surface. Moreover, since a monomolecular layer is an extremely fine layer, a finer pattern can be formed.

In a more preferred embodiment of a cell culture plate provided by the present invention, the water droplet contact angle of the water-repellent surface exceeds 150°. In a more preferred embodiment of the method for producing a cell culture plate described herein, the water-repellent layer is formed such that the water droplet contact angle of the water-repellent surface exceeds 150°. By forming such an ultra-water-repellent surface, a cell culture product in a finer and more defined pattern can be obtained. Therefore, in another aspect, the present invention provides a method for producing a cell culture product wherein the water droplet contact angle of the water-repellent surface exceeds 150°.

In another preferred embodiment of a cell culture plate provided by the present invention, the hydrophilic surface is formed in a three-dimensionally shaped pattern. In another preferred embodiment of the method for producing a cell culture plate described herein, the hydrophilic surface is formed into a three-dimensionally shaped pattern. The "three-dimensionally shaped pattern" here refers to a pattern with a shape (form) that extends in a plane (two-dimensional direction) and, in addition, at least in the height direction with respect to the plane, but the degree of the extension is not limited. For example, a part of the water-repellent layer is removed by lithography in the thickness (depth) direction, and the groove pattern formed thereon having a prescribed depression is a typical example included in the three-dimensionally shaped pattern. By constituting a hydrophilic surface of such three-dimensionally shaped pattern, can be produced a desired three-dimensionally shaped cell culture product that is formed precisely according to the pattern. Therefore, as another aspect, the present invention provides a method for producing a cell culture product, wherein the above-mentioned culture medium is disposed in the three-dimensionally shaped pattern and the cell culture product is formed in the three-dimensional shape corresponding to the pattern.

In a particularly preferable embodiment of a cell culture plate provided by the present invention, the hydrophilic surface is constructed to form a groove or line pattern of a width of 100 µm or less. In another particularly preferred embodiment of the method for producing a cell culture plate described herein, the hydrophilic surface is formed in a groove or line pattern of a width of 100 µm or less. By constructing a hydrophilic surface of such a pattern, for example, a cell culture product patterned in a tubular shape, such as a capillary network with a prescribed pattern desirable in regenerative medical practice, can be favorably produced. Therefore, as another aspect, the present invention provides a method for producing a cell culture product, wherein the above-mentioned hydrophilic surface is formed in a groove or line pattern of a width of 100 µm or less, and a tubular cell culture product corresponding to the pattern is favorably produced.

In another preferred embodiment of the method for manufacturing a plate described herein, the water-repellent layer is constituted with an high-molecular-weight organic compound having an alkyl group, alkenyl group or alkynyl group substituted or not substituted with a functional group that can be bonded to the plate.

Such high-molecular-weight organic compound, by having a functional group that can be bonded to the plate, can readily form an organic compound layer on the plate surface. Further, by having a substituted or non-substituted alkyl group, alkenyl group or alkynyl group, the high-molecular-weight organic compound may achieve high hydrophobicity (therefore, ultra water-repellent property) with a water contact angle of, for example, 130° or greater, and more preferably 150° or greater. Therefore, the organic-compound-layer surface formed can be furnished with a desirable water-repellency (ultra water-repellency) so that aqueous medium (culture solution) or adherent cells cannot adhere thereto.

In such embodiment, it is more preferable that the alkyl group, alkenyl group or alkynyl group be partially or completely substituted by fluorine. By forming a hydrophobic organic compound layer (water-repellent layer) from a compound having a fluorine-substituted carbon chain, the water-repellency on the surface can be improved. Hence, an ultra water-repellent region can be formed on the surface of the plate. A monomolecular layer composed of an above-described organic compound is particularly preferable to be used as the water-repellent layer, and an approximately uniform ultra water-repellent region can be formed over the entire surface of the plate.

Furthermore, in another aspect, the present invention provides a cell culture product shaped or organized into a desired fine pattern. The cell culture product with such a structure can be obtained by either one of the methods described herein. It is preferable that the dimensions of the pattern may be controlled at micro-level (typically between greater than or equal to 1 µm, but less than 1 mm) or milli-level (typically between greater than or equal to 1 mm, but less than 10 mm). As a preferable embodiment, the cell culture product provided is formed in a desired three-dimensional pattern. Alternatively, a patterned tubular or string-like cell culture product such as a capillary network or neural network, is provided.

BRIEF DESCRIPTIONS OF THE DRAWINGS

FIG. 1 is a drawing illustrating a process for forming a water-repellent layer and a hydrophilic surface on a plate. Specifically, FIG. 1(1) represents a surface of the plate, wherein various reactive groups (surface functional groups) are introduced thereto; FIG. 1(2) represents a state in which a water-repellent layer is formed on the plate surface; and FIG. 1(3) represents a state in which a hydrophilic surface with a predetermined pattern is formed.

FIG. 2(2) represents a state in which excess medium has been removed.

FIG. 3(2) represents a state in which the plate has been removed from the medium.

BEST MODE FOR CARRYING OUT THE INVENTION

Figure 1:
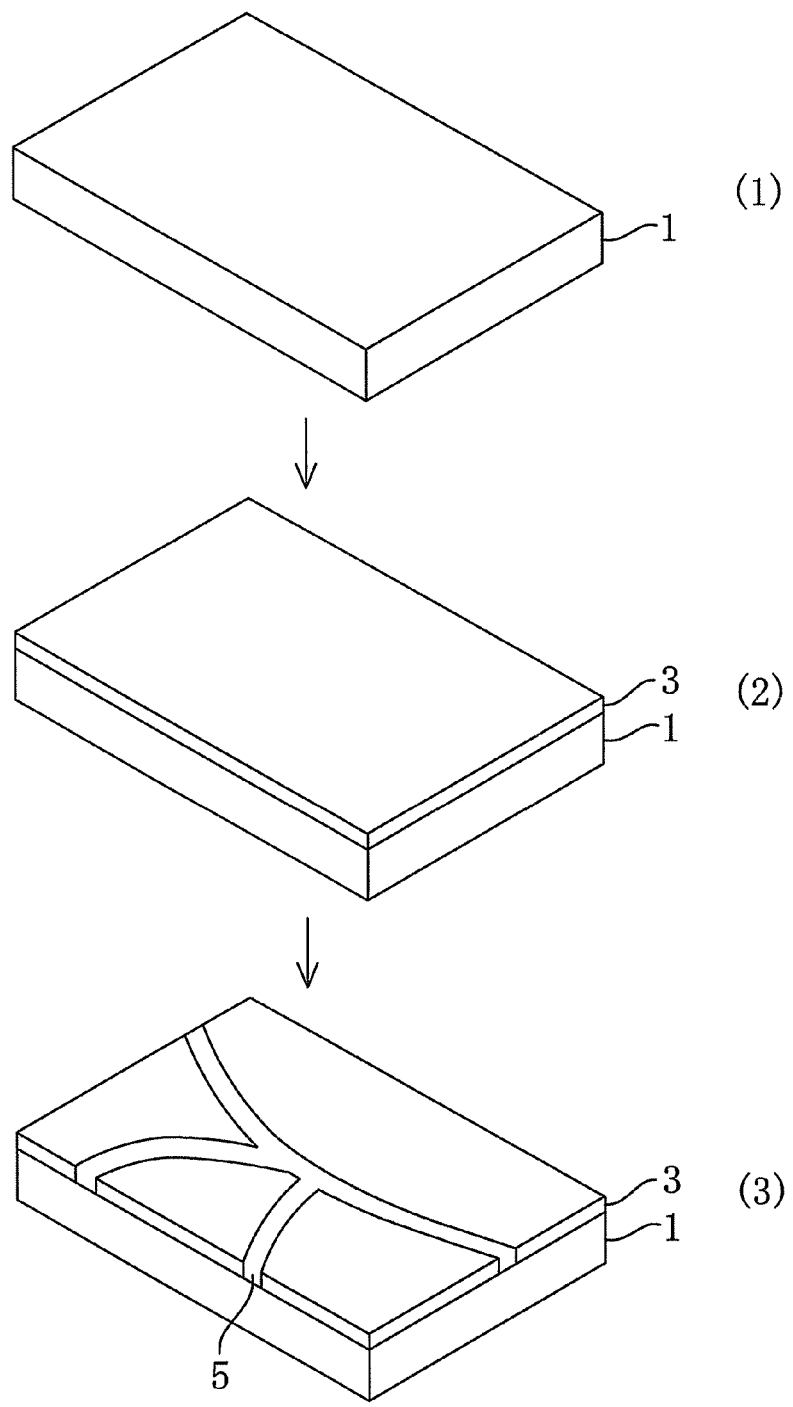

Hereinafter, preferred embodiments of the present invention will be described. The matters other than those specifically mentioned in this specification (for example, composition of hydrophilic surface and water-repellent surface on a cell culture plate, pattern of hydrophilic surface, and lithography technique applied), but necessary for performing the present invention (for example, cells to be cultured, culture medium, method for cell culture, and means for forming a water-repellent layer), can be considered as matters of design by those skilled in the art based on the conventional technology in this field. The present invention can be performed based on the contents described in this specification and the common technical knowledge in the field.

Various conventionally known substrates used for cell culture can be employed as the substrate used for manufacturing a cell culture plate (in other words, a plate for producing cell culture products) described herein with no particular limitation. For example, as a material constituting the substrate can be used glass, silicon, ceramics, metal and high-molecular-weight materials. A general cell culture plate made of silica glass (for example, Petri dishes) can be favorably utilized. A ceramics substrate made of, for example, silica, alumina or apatite, can also be used as a preferable material. A metal substrate made of, for example, gold, silver or copper, can also be used as a preferable material. Further, a high-molecular-weight substrate made of, for example, polyacetal resin, polyamide, polycarbonate, ABS resin, polyimide, fluorine-based resin, polyethylene, polypropylene, polystyrene, or derivatives of these materials, can also be used as a preferable material. Moreover, a substrate made of synthetic resin of these materials or a substrate made of silk fibroin film may also be utilized.

Among these, those that facilitates formation of a water-repellent layer can be utilized favorably. Specifically, a plate made of silicon or silica is preferable because a reactive group (typically a hydrophilic group such as silanol group) that effects bonding of a high-molecular-weight compound to the surface may be easily introduced to the surface, and a layer of various high-molecular-weight compounds can be easily formed. For example, by applying various treatments to a silicon substrate having a surface oxidation layer (silica layer), silanol group (Si—OH) can be introduced to the surface.

On the other hand, a water-repellent layer can be formed with various conventionally known high-molecular-weight compounds (typically light-sensitive resin) that allow removal (including modification or destruction at the molecular level) of at least the surface of the layer by an appropriate lithography technique or abrasion technique. For example, a high-molecular-weight substance having a functional group capable of bonding to the substrate and a substituted or non-substituted alkyl group, alkenyl group or alkynyl group (a relatively long carbon chain with the number of C being 1 or more, preferably the number of C being 5 or more, for example between 10-30) can be utilized favorably.

When a compound having such alkyl (or alkenyl or alkynyl) chain is bonded to the surface of the substrate, a highly oriented, high density monomolecular layer (hence, self-assembled monolayer) may be readily formed due to the van der Waals force between such chains, and thus is preferable. Moreover, since an alkyl group (for example, the number of C being between 1-30, or more preferably the number of C being between 10-30) may exhibit high hydrophobicity (water-repellency), it is particularly preferable.

For example, in the case of a silicon substrate, wherein the surface (culture bed) is furnished with silanol groups, preferable as the compound constituting the water-repellent layer is an organic silicon compound having a functional group, such as methoxy group, capable of bonding to the culture bed (preferably to bond to the reactive group on the surface of the culture bed); and having a relatively long main chain or side chain. For example, alkyltrialkoxysilane represented by general formula $C_nH_{2n+1}Si(OC_mH_{2m+1})_3$ (preferably n being a natural number selected from between 10-30, and m being 1 or 2) is a preferable compound.

Further, examples of other preferable compounds include organic compounds having a functional group that can be bonded to the substrate, and an alkyl group, alkenyl group, alkynyl group or the like being partially or entirely substituted by fluorine. Compound having a relatively long alkyl (or alkenyl or alkynyl) chain may readily form a monomolecular layer, and thus is particularly preferable.

Although not limited specifically, the degree of fluorine substitution is preferable to be such that more than half (for example, 70% or more of the number of hydrogen atoms) or substantially all the hydrogen atoms constituting the alkyl chain are substituted with fluorine atoms. For example, in the alkyltrialkoxysilane represented by the general formula, it is preferable that 70% or more of the number of hydrogen atoms constituting the alkyl chain be substituted with fluorine atoms (see examples described below).

Any conventionally known method can be used as a means for forming a hydrophobic organic compound, which serves as the water-repellent layer having a water-repellent surface on the surface of the substrate (culture bed).

Typically, as represented in FIG. 1(1), activation treatment, such as chemical treatment, plasma treatment, ultraviolet light irradiation treatment and the like, is first applied to the surface of a substrate 1, and various reactive groups (surface functional groups) for chemically bonding an organic compound layer to the surface of the substrate 1 are then introduced to the surface of the substrate 1. For example, in the case where the substrate 1 is of silicon, the surface of the substrate 1 may be hydrophilized by irradiating vacuum ultraviolet light (specifically, by introducing silanol group, i.e., hydroxyl group), preferably, for example, in the atmosphere or under reduced pressure. Further, in the case where the irradiation treatment is performed in an atmosphere containing oxygen, organic matters remained on the surface of the substrate 1 can be removed by ozone generated from the ambient oxygen upon the ultraviolet light irradiation.

Next, as represented in FIG. 1(2), the activated substrate 1 is treated in a vapor phase of organic compound such that the organic compound is grown on the substrate 1, to form a water-repellent layer 3 (see examples described below). It is preferable to employ plasma CVD method, where a gas composed of the organic compound is excited to plasma state and a thin film is formed by chemical reactions in the vapor phase as well as on the substrate surface utilizing the activated plasma. According to this method, a water-repellent surface (water-repellent layer) can be formed on the surface of the substrate under at around room temperature. Therefore, it is favorable for forming a water-repellent layer on a substrate made of, for example, a high-molecular-weight material (synthetic resin) with low heat resistance (for example, Petri dish made of polystyrene).

The water-repellent layer 3 is preferably made of a monomolecular layer, wherein an organic compound is orientated in a prescribed direction. By being a monomolecular layer, the water-repellent layer can be uniform in thickness and ultra thin as well. This effects uniform water-repellency and formation of a ultra fine pattern. In the case where the water-repellent layer 3 grows beyond the monomolecular layer, as desired, the molecules deposited in excess can be removed to form a monomolecular layer. The method for forming such monomolecular layer is not limited specifically, and can be carried out by appropriately combining acid treatment, alkaline treatment, aqueous wash and the like according to the substance used.

It is preferable to form a water-repellent surface having a contact angle of 120° or greater, where the contact angle is the angle formed by the surface of the water-repellent layer 3 and a water droplet (hence the water droplet contact angle). More preferable is 140° or greater, and particularly preferable is 150° or greater (for example between 150°-160°). A water-repellent surface with such a high contact angle can maintain a relatively high volume of a liquid droplet (water droplet) composed of a common medium in a near spherical shape. The contact angle can be measured by various conventionally known means. For example, the static contact angle of water droplet composed of distilled water (for example, approximately 2 mm in liquid droplet diameter) can be measured by drop method in an atmosphere at 25° C. using a contact angle goniometer (for example, "CA-X150" available from Kyowa Interface Science Co., Ltd.).

Next, as represented in FIG. 1(3), a hydrophilic surface 5 in a prescribed pattern is formed by removing the part of the water-repellent layer 3 corresponding to the pattern, using various techniques, for example lithography. For example, it is preferable to apply photolithography. For example, a photo mask formed with a transmitting portion (light-transmittable opening) matching the prescribed pattern is prepared, and a high energy light (for example, vacuum ultraviolet light) from a prescribed light source (for example, excimer lamp) is emitted through the photo mask. Accordingly, as described in the examples below, only the part irradiated with the light or the pattern portion of the water-repellent layer 3 (at least its surface portion) can be selectively removed by photochemical reaction (including decomposition and modification). At the same time, with this treatment, the surface of the substrate 1 is activated and various hydrophilic groups can be introduced to the surface 5. For example, in the case where the substrate is of silicon, while the water-repellent layer 3 is removed preferably, for example, by irradiating vacuum ultraviolet light in the atmosphere or under reduced pressure, the surface 5 of the substrate 1 can be concurrently hydrophilized (specifically, with introduction of silanol group, i.e., hydroxyl group).

As a result, the hydrophilic surface 5 in a prescribed pattern can be formed. In other words, in a preferred embodiment of the present invention, lithography effects removal of the water-repellent layer 3 and formation of the hydrophilic surface 5 on the removed surface of the substrate 1 at the same time. In the case where the hydrophilicity of the surface of the substrate 1 is insufficient, hydrophilicity can be added or improved by performing further chemical treatment. The lithography is not limited to photolithography, and a conventionally known lithography can be employed. Preferred examples include electron beam lithography, EUV (Extreme Ultraviolet light with a wavelength of around 13.5 nm) lithography and convergence ion beam lithography.

The pattern formed by lithography can be of any shape and has no specific limitation. Specifically, the pattern may be of a planar or three-dimensional structure, and may be of an organized or random structure. The planar structure includes patterns composed of lines and spaces, polka-dots, lattice, lines or grooves imitating a complex branching structure of blood vessels, or the like. The three-dimensional structure can be tubular (including a branching structure), depressed (particularly, line grooves having a semicircle cross-section), bulged (particularly hemispherical), or constructed to form patterns of various living tissues (or organs) or the like. Alternatively, according to the plate provided by the present invention, since the culture medium and cells disposed on the surface; and the water-repellent surface of the plate may strongly repel each other, the medium or adherent cells can be disposed in a three-dimensional pattern (typically, as protruding droplets) on the hydrophilic surface. Therefore, a cell culture product can be three-dimensionally formed (produced) in the medium disposed in such a three-dimensional pattern.

The size of the pattern (for example, the width of a groove pattern, the diameter of a dot pattern) has no specific limitation and can be chosen as desired. For example, in the case of a (line) groove pattern, a fine pattern of a width of 10 mm or less, preferably 3 mm or less, more preferably 1 mm or less, still more preferably 500 µm or less, still more preferably 100

μm or less, and particularly preferably 50 μm or less, can be formed by employing a lithography technique.

Cells to be cultured are not specifically limited and desired culturable cells (typically, eukaryotic cells such as mammalian cells) can be utilized with no specific limitation. Particularly, adherent cells found in various living tissues, such as epithelial cells, fibroblasts, vascular endothelium cells, hepatocytes or cancerous cells, can be cultured as aligned in a prescribed pattern or molded into a prescribed pattern. In addition, various floating cells, such as embryonic stem cells (ES cell) or bone marrow stem cells can also be cultured efficiently in droplets of culture medium disposed on a prescribed pattern.

Therefore, according to the method for producing a cell culture product described herein, the following cell culturing is possible. (1) Culturing epithelial cells or fibroblasts into a prescribed pattern; (2) culturing a plurality of cell types included in hepatocytes or osteoblasts into a prescribed pattern in a prescribed array; (3) culturing vascular endothelium cells into a three-dimensional tubular structure similar to the fine, complex structure of blood vessels; and (4) culturing stem cells such as embryonic stem cells into a fine mass.

Various conventionally known media can be utilized with no specific limitation as a culture medium for such cell culture. For example, Eagle medium, RPMI medium, Ham's medium, Fisher's medium or MCDB medium of various compositions can be utilized. Eagle medium includes BM medium, MEM medium, DMEM medium or the like. Further, 5 to 10% of serum may also be added to these media. Among these media, Eagle medium is particularly preferable for culturing mammalian cells.

Figure 2:
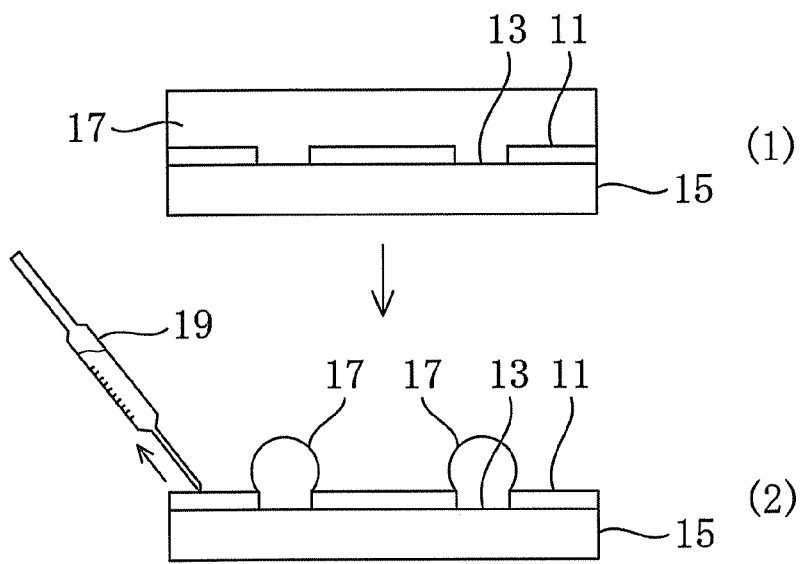
FIG. 2 is a drawing illustrating a procedure for disposing culture medium on a hydrophilic surface. Specifically, FIG. 2(1) represents a state in which the medium has been disposed on the plate.

There is no specific limitation on the method for disposing medium on the hydrophilic surface. Preferably, as illustrated in FIG. 2(1), medium 17 may be supplied (poured) onto a substrate 15 such that the entire surface of the substrate 15 including a water-repellent surface 11 and a hydrophilic surface 13 is covered. Alternatively, after the medium is supplied, the medium 17 in excess can be removed by suction with a pipette 19 or the like in the direction of the arrow as illustrated in FIG. 2(2), so that the medium 17 may be placed only on the hydrophilic surface 13.

Figure 3:
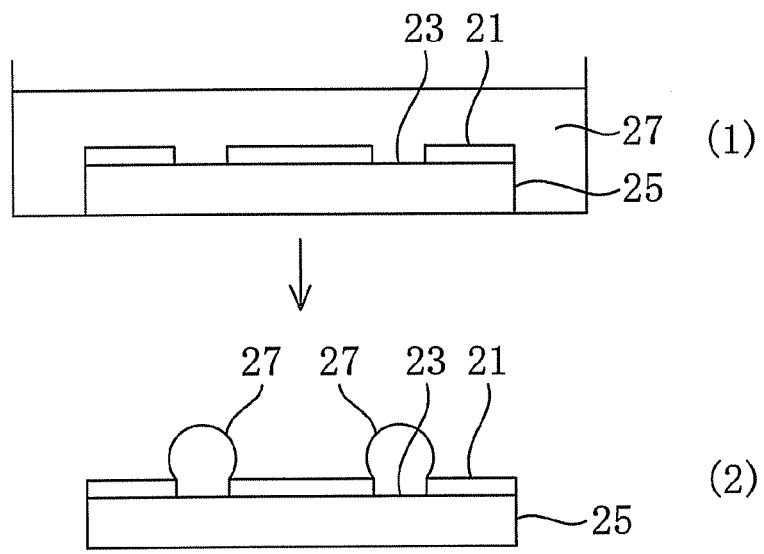
FIG. 3 is a drawing illustrating another procedure for disposing culture medium on a hydrophilic surface. Specifically, FIG. 3(1) represents a state in which the plate has been submerged in the medium (liquid)

As illustrated in FIG. 3(1), the entire surface of a plate 25 including a water-repellent surface 21 and a hydrophilic surface 23 can be submerged in medium 27. Thereafter, as illustrated in FIG. 3(2), the plate 25 is removed from the medium 27. Here, since the medium 27 (17 in FIG. 2(1)) is repelled from the water-repellent surface 21 (11 in FIG. 2(1)) on the plate 25 (15 in FIG. 2(1)) for cell culture, the medium 27 (17 in FIG. 2(1)) may be selectively disposed on the hydrophilic surface 23 (13 in FIG. 2(1)) with distinct boundaries.

Figure 4:
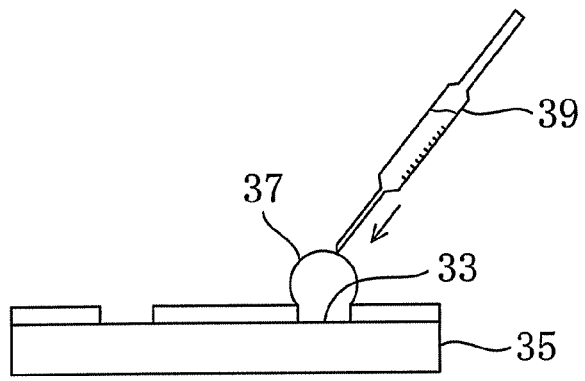
FIG. 4 is a drawing illustrating another procedure for disposing culture medium on a hydrophilic surface.

Alternatively, as illustrated in FIG. 4, medium 37 can be disposed along a hydrophilic surface 33 in a prescribed pattern on a plate 35 in the direction of the arrow using a pipette 39 or the like.

There is no specific limitation on the method for culturing cells in the medium. Therefore, the culturing method or culturing conditions can be appropriately selected according to the cells to be cultured or to the pattern. For example, the composition or concentration of the medium, the culturing temperature or culturing time period or the like may be selected appropriately. In the case of general mammalian cells, such as vascular endothelium cells, epithelial cells, fibroblasts or embryonic stem cells, a cell culture product in a desired pattern can be produced by culturing at a temperature ranging from room temperature to the body temperature of the mammal (i.e., 20° C. to 40° C., preferably 33° C. to 38° C.) for a period ranging from half a day to four days, or longer (for example, seven to fourteen days). Further, in order to prevent the pH value of the medium from increasing, it is preferable to carry out cell culture in a $CO_2$ incubator that maintains the $CO_2$ concentration in the cell culturing atmosphere approximately constant (for example, at 3% to 10%, particularly at about 5%).

The present invention is further described in details by the following examples, but the examples only serve to illustrate, and not restrict the present invention.

EXAMPLES

Example 1

<1> Manufacturing of Cell Culture Plate (i) Treatment of Substrate:

The surface of a substrate was washed and subjected to hydrophilization according to a method disclosed in the following literature.

'Surface and Interface Analysis', Vol. 34, No. 1, pp. 550-554, 2002.

First, a 2.5 cm×5 cm-size Petri dish made of silica glass was prepared as a substrate for cell culturing. The substrate (Petri dish) may be used without any treatment, but in the present example, a reactive group was intentionally introduced onto the surface of the substrate as follows.

The surface of the substrate was exposed to vacuum ultraviolet radiation (VUV) generated by excimer lamp (Ushio Electric, Inc., UER20-172V model, wavelength $\lambda=172$, output 10 mWcm$^{-2}$ work density) for approximately 10 minutes. In the present example, the spatial distance between the lamp and the substrate was approximately 10 mm. The oxygen molecules in the atmosphere were photoexcited by the VUV irradiation to generate atomic oxygen and ozone (hereinafter, "reactive oxygen species"). On the other hand, organic molecules as impurities that may potentially exist on the substrate surface decomposed because of dissociative activation of the carbon-carbon and carbon-hydrogen bonds and oxidation caused by the reactive oxygen species generated. In other words, irradiated with the light, the substrate surface was washed by the photochemical elimination reactions of the organic molecules on the substrate surface. By the above treatment, hydroxyl group (silanol group) preferable for forming an high-molecular-weight organic compound layer, which is described later, was introduced to the surface of the substrate (Petri dish).

(2) Forming of Water-Repellent Layer:

A high-molecular-weight organic compound, a fluoroalkylsilane here, in particular, heptadecafluoro-1,1,2,2-tetrahydro-decyl-1-trimethoxysilane (available from Shin-Etsu Chemical Co., Ltd.) represented by $F_3C(CF_2)_7(CH_2)_2Si(OCH_3)_3$, was used. The surface-treated substrate was introduced into a vacuum chamber, and plasma CVD was carried out at a temperature of 50° C. or below, and at the entire pressure (hence Ar excitation gas and source gas) within the chamber set to between 65 and 95 Pa. Accordingly, on the substrate surface, was formed a polysiloxane film with methyl groups serving as a terminal functional group. The contact angle of the substrate surface after the treatment was equal to 150° or exceeding 150° (>150°). Note that the terminal chemical functional groups on the above-described film surface can be controlled by self-organization process. For example, the surface-treated substrate was hydrophilized (see the literature above), and was placed into a 300 cm$^3$ Teflon™ container along with a glass cup filled with approximately 0.02 cm³ of a solution of the high-molecular-weight organic compound. The resulting container was sealed; and then placed and stored over three hours in a furnace maintained at 150° C.

Figure 5:
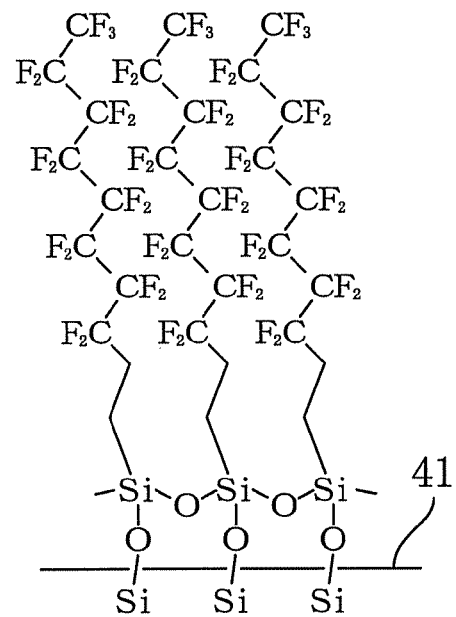
FIG. 5 is a drawing illustrating an example of a chemical structure constituting a water-repellent layer.

With such treatment, elimination reaction (de-alcoxylation reaction) occurs between the terminal hydroxyl group on the substrate surface and the methoxy group of heptadecafluoro-1,1,2,2-tetrahydro-decyl-1-trimethoxysilane, and also within the methoxy groups; and as illustrated in FIG. 5, a polysiloxane film with fluorine-substituted alkyl side chains is formed on the surface of the substrate (Petri dish) 41.

As illustrated in the drawing, the side chains of such film forms a monomolecular layer extending in an uniaxial direction, and this monomolecular layer corresponds to the water-repellent layer related to the present example. The static contact angle of distilled water (approximately 2 mm in liquid droplet diameter) on the surface of the water-repellent layer was measured by drop method under an atmosphere at 25° C. using a contact angle goniometer (for example, "CA-X150" available from Kyowa Interface Science Co., Ltd.). The droplet contact angle exceeded 150° and exhibited extremely high water-repellency (ultra water-repellency).

Figure 6:
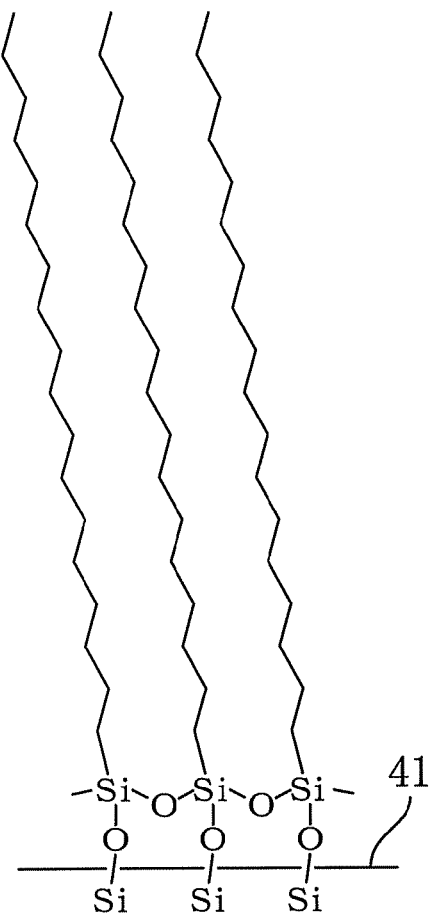
FIG. 6 is a drawing illustrating another example of a chemical structure constituting a water-repellent layer.

Note that alkyltrialkoxysilanes, particularly n-octadecyl trimethoxysilane (available from Tokyo Chemical Industry Co., Ltd.) represented by $H_3C(CH_2)_{17}Si(OCH_3)_3$ can be used instead of the above fluoroalkylsilane. In such case, elimination reaction (de-alcoxylation reaction) occurs between the terminal hydroxyl group and the methoxy group of n-octadecyl trimethoxysilane, and also within the methoxy groups, and as illustrated in FIG. 6, a polysiloxane film with 18-carbon-long alkyl side chains is formed on the surface of the substrate 41. As illustrated in the drawing, the side chains of the film form a monomolecular layer extending in an uniaxial direction. The surface of the monomolecular layer also exhibits extremely high water-repellency (ultra water-repellency).

Figure 7:
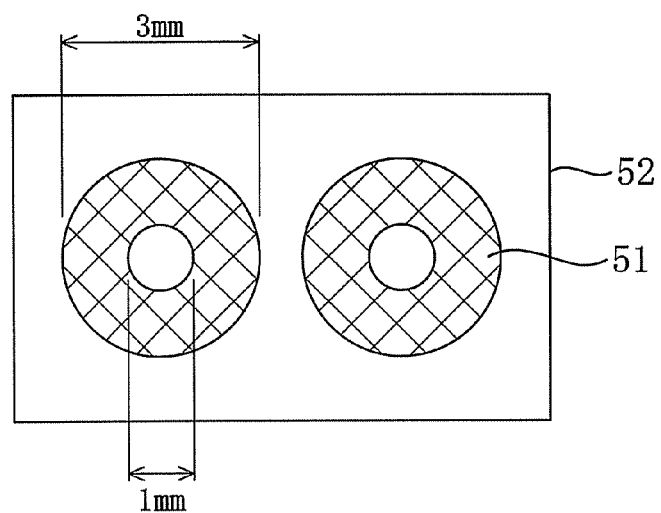
FIG. 7 represents a mask used in photolithography in an example.

(3) Patterning of Water-Repellent Layer (Lithography Treatment):

The water-repellent layer was micro-processed by general photolithography method. As illustrated in FIG. 7, was prepared a photomask 52 including a ultraviolet-light blocking Cu mesh portion 51 (here referring to the two doughnut-shaped portions with an inner diameter of 1 mm and an outer diameter of 3 mm).

Next, the surface of the substrate 41 was irradiated through the Cu mesh photomask 52 with excimer light having a wavelength of 172 nm. Accordingly, the water-repellent layer in the portion of the surface of the substrate 41 other than the portion corresponding to the Cu mesh portion 51 was decomposed and removed by the light energy of the irradiating excimer light.

Figure 8:
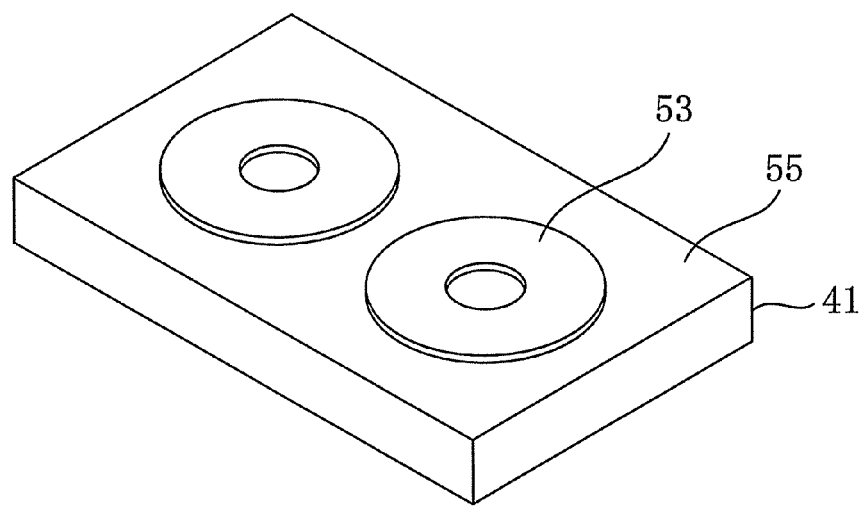
FIG. 8 is a schematic diagram representing an example of a plate composed of a water-repellent layer and a hydrophilic surface.

As a result, as illustrated in FIG. 8, was formed on the surface of the substrate 41 a pattern of a water-repellent surface and hydrophilic surface. That is to say that a doughnut patterned water-repellent layer (water-repellent surface) 53 corresponding to the Cu mesh portion (doughnut-shaped portion) 51 of the photomask 52 was retained while a hydrophilic surface 55 corresponding to the other portion was formed.

<2> Production of Fibroblast Culture Product (1) Cells Cultured

Mouse fibroblasts (NIH/3T3) purchased from American Type Culture Collection (ATCC) were used.

(2) Medium

Medium composed of the following was prepared.

MEM; Minimum Essential Medium: 9.53 g/L
HEPES buffer; 2-[4-(2-hydroxyethyl)-1-piperazinyl] ethanesulfonic acid: 5.96 g/L
$NaHCO_3$: 2.20 g/L
Penicillin-Streptomycin: 1%
MEM Non-Essential Amino Acids Solution: 1%
FBS; Fetal bovine serum: 10%

(3) Culturing Method

The substrate 41 (see FIG. 8) obtained in the above <1> was completely submerged in the medium of the above composition in a similar way as FIG. 3. Thereafter, the substrate 41 was promptly removed from the medium so that the medium was selectively disposed on the hydrophilic surface 55 formed in the areas other than the prescribed doughnut-shaped portion.

Next, the purchased mouse fibroblasts were gently disposed in the medium placed in the prescribed pattern (hence, in the portion other than the doughnut-shaped portion) on the substrate 41. The culturing was carried out at 37° C. and approximately 5% $CO_2$ partial pressure in a $CO_2$ incubator. To prevent drying of the medium, medium was added accordingly with a pipette and the incubation was carried out for three days.

<3> Observation of Cell Culture Product

Figure 9:
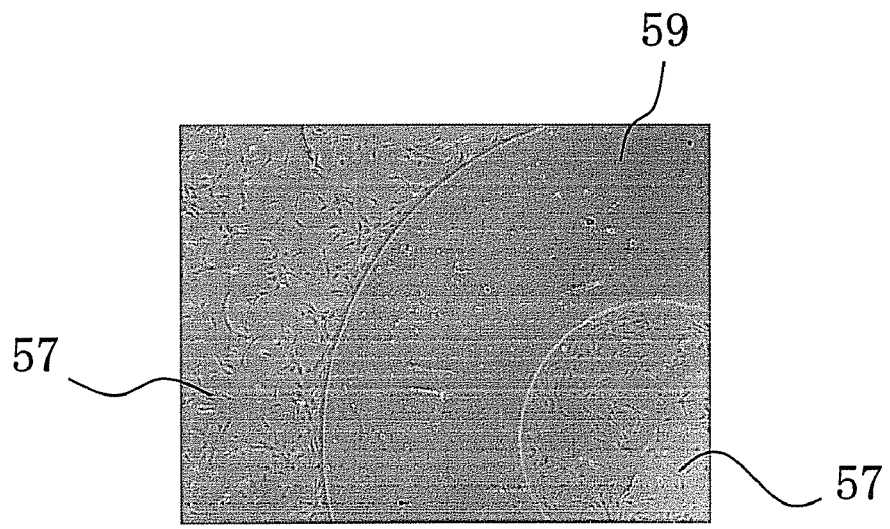
FIG. 9 is a phase-contrast microscope photo showing a part of a cell culture product (one day after culture initiation) produced in an example.
Figure 10:
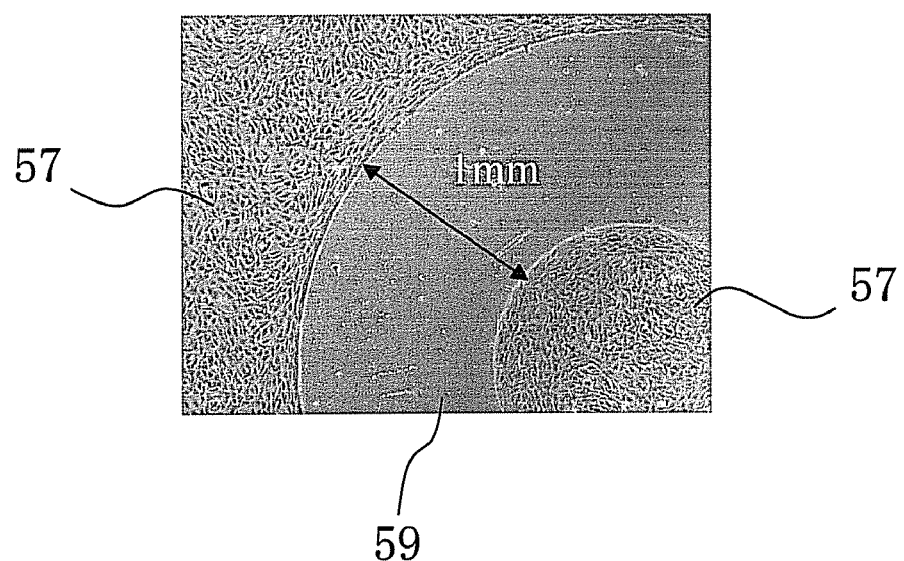
FIG. 10 is a phase-contrast microscope photo showing a part of a cell culture product (three days after culture initiation) produced in an example.
Figure 11:
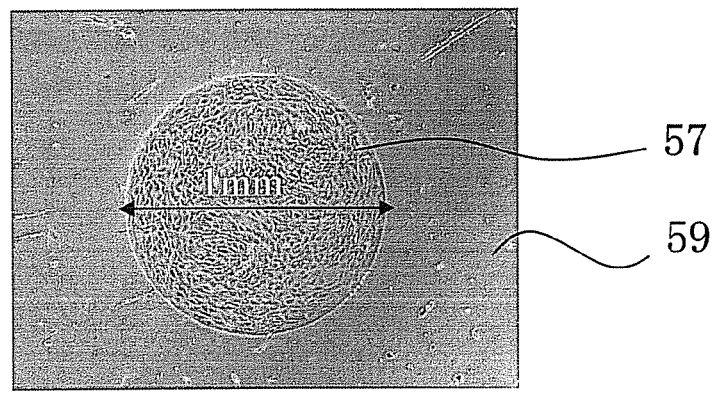
FIG. 11 is a phase-contrast microscope photo showing a part of a cell culture product (three days after culture initiation) produced in an example.
Figure 12:
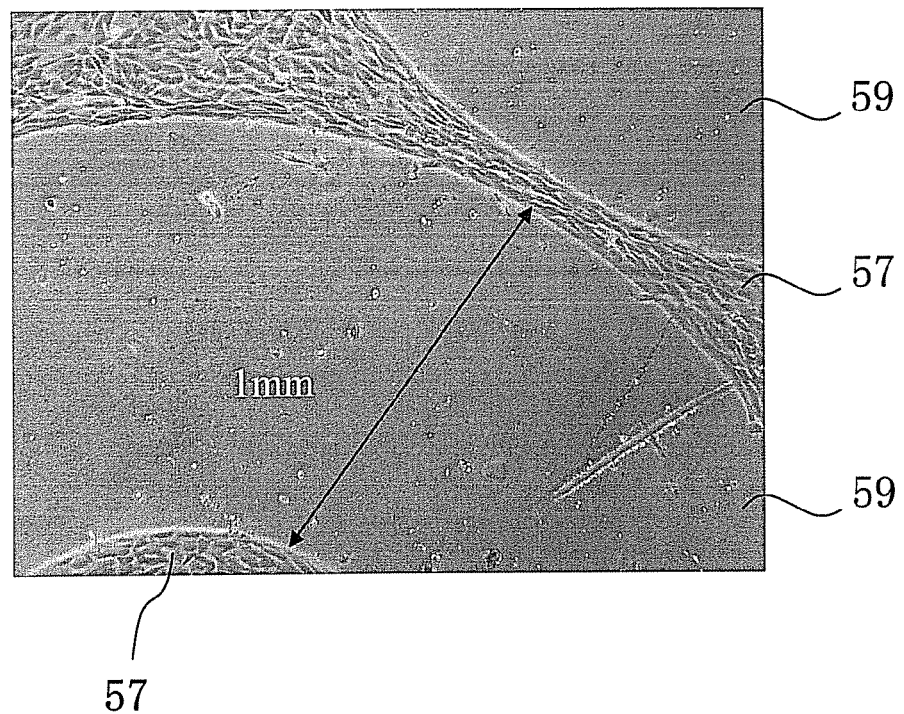
FIG. 12 is a phase-contrast microscope photo showing a part of a cell culture product (three days after culture initiation) produced in an example.

The culture product was observed at the first day and the third day with a phase contrast microscope (model "IX70", available from OLYMPUS corporation). The results are illustrated in FIGS. 9, 10, 11 and 12. FIG. 9 represents a microphotograph showing a culture product 57 (a portion in the periphery of the doughnut-shaped water-repellent layer 59 on the substrate) at the first day of culturing. FIG. 10 represents a microphotograph showing the culture product 57 at the third day of culturing. FIG. 11 represents a microphotograph around the centre-circle portion (culture product 57) of the doughnut-shaped water-repellent layer 59. FIG. 12 represents a microphotograph showing the culture product 57 around the boundary between the two doughnut-shaped water-repellent layers 59.

As illustrated in FIG. 9, from the first day of culturing, the cell growth can be observed only in the areas other than the doughnut-shaped water-repellent layer 59, and as illustrated in FIGS. 10, 11 and 12, it is evident that on the third day of culturing, the cell culture product 57 has grown with a distinct boundary in the portion other than the doughnut-shaped water-repellent layer 59.

Example 2

<1> Production of Vascular Endothelium Cell Culture Product

Figure 13:
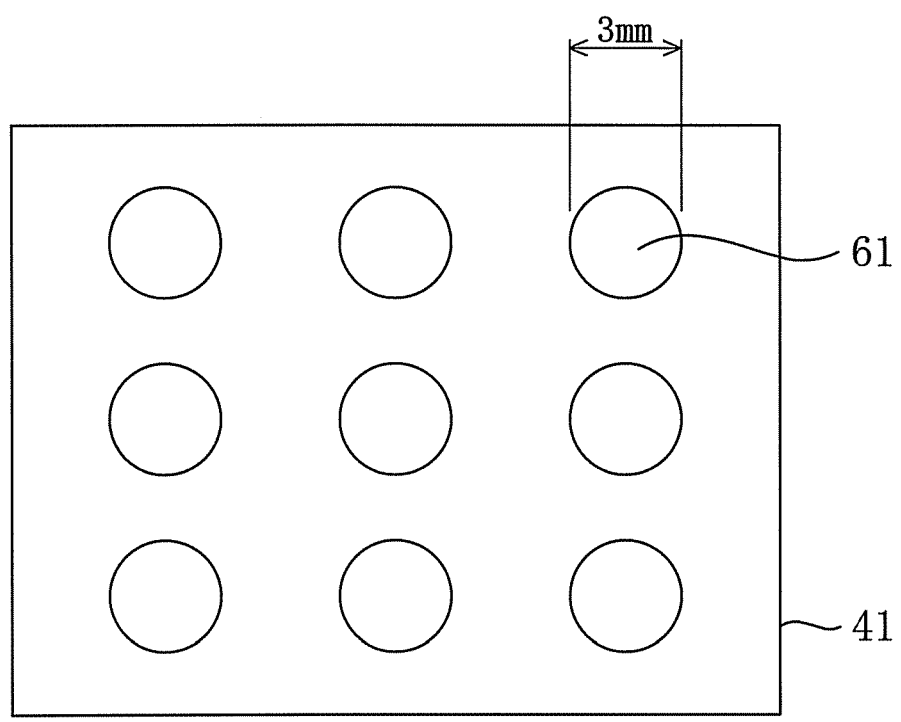
FIG. 13 is a schematic diagram representing a pattern employed in an example.

Instead of the "the portion other than the doughnut-shape" of Example 1, "the pattern composed of a hydrophilic surface" on the substrate 41 in this example was a "pattern composed of dots" with a diameter of approximately 3 mm as illustrated in FIG. 13 and cells were cultured on the dot pattern 61. As for the cells, normal human umbilical vascular endothelium cells (HUVEC) purchased from Kurabo Industries Ltd. were used, and for the medium, "HuMedia-EG2", a low blood serum liquid medium for culturing normal HUVEC, purchased from Kurabo Industries Ltd. was used. Except for these conditions, a cell culture product was produced in a similar manner as Example 1.

<2> Observation of Cell Culture Product

Figure 14:
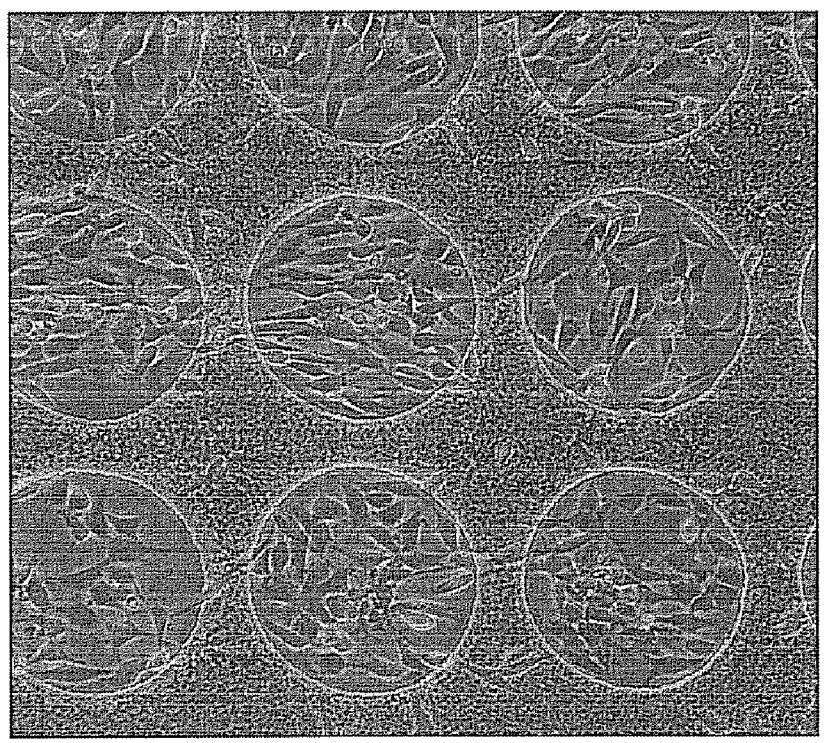
FIG. 14 is a phase-contrast microscope photo showing a part of a cell culture product (three days after culture initiation) produced in an example.

The culture product was observed at the third day of culturing with a phase contrast microscope similar to the aforementioned. The results are illustrated in FIG. 14. As clearly shown in FIG. 14, having distinct boundaries, the cells were grown in the plurality of dots with a diameter of approximately 3 mm, and cell culture products were produced according to the pattern.

Some Preferable Embodiments

A few specific embodiments of the present invention, apart from Examples 1 and 2, will be described below.

Figure 15:
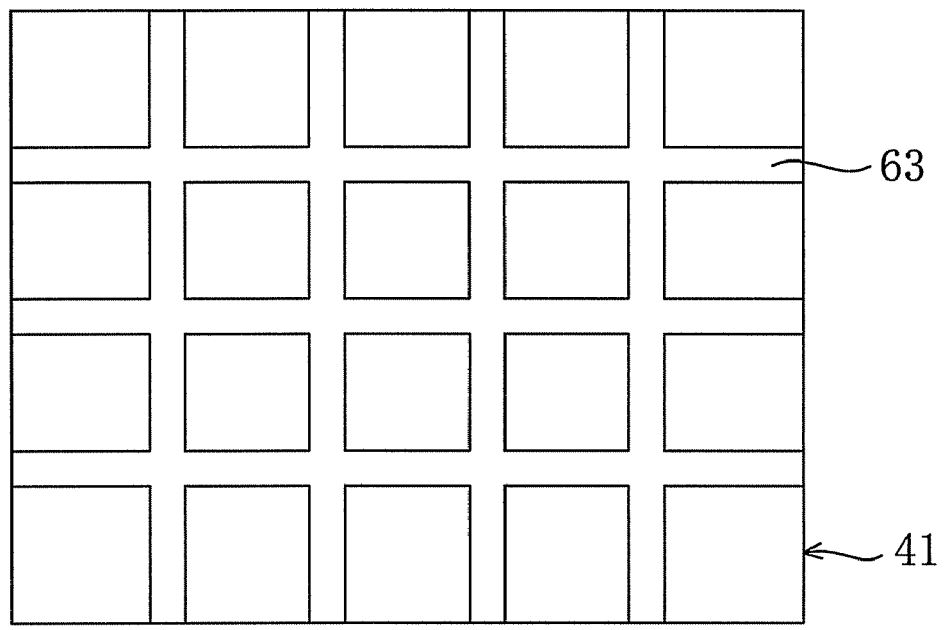
FIG. 15 is a schematic diagram representing an example of a pattern that may be formed on a plate.
Figure 16:
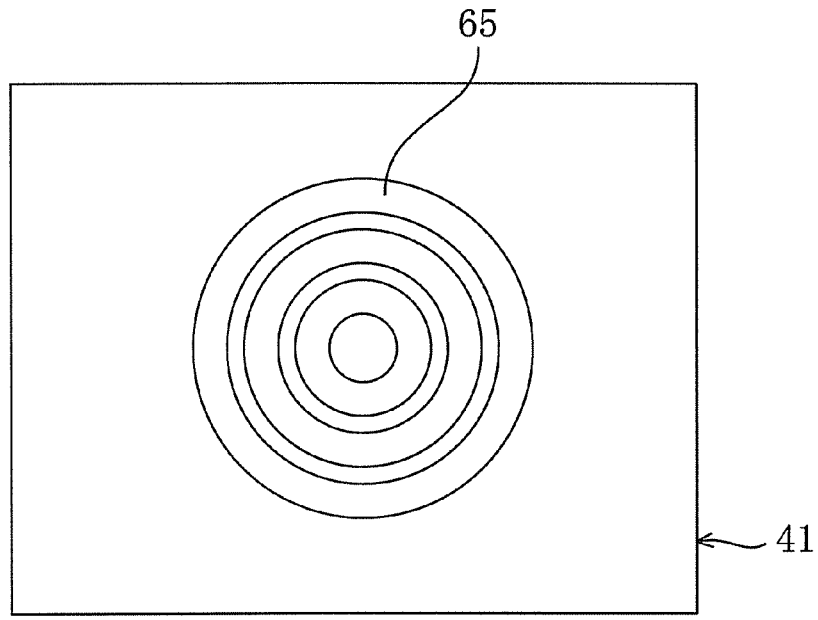
FIG. 16 is a schematic diagram representing another example of a pattern that may be formed on a plate.
Figure 17:
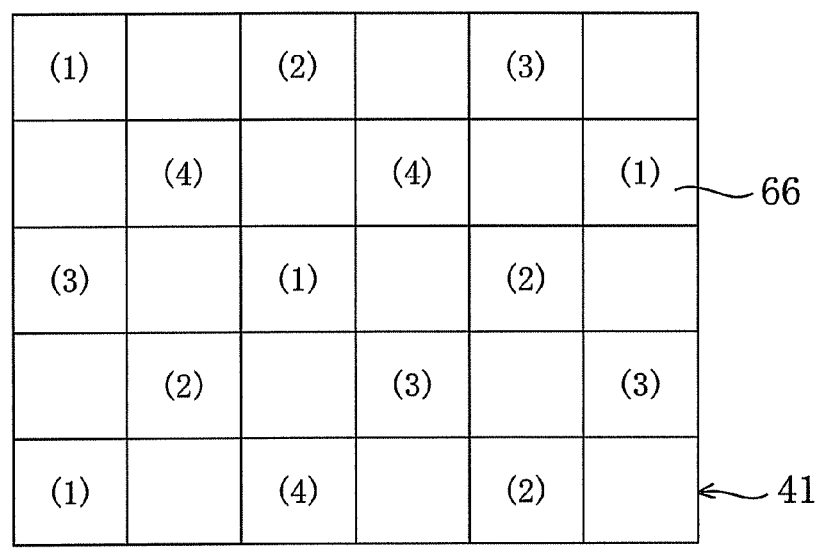
FIG. 17 is a schematic diagram representing another example of a pattern that may be formed on a plate.
Figure 18:
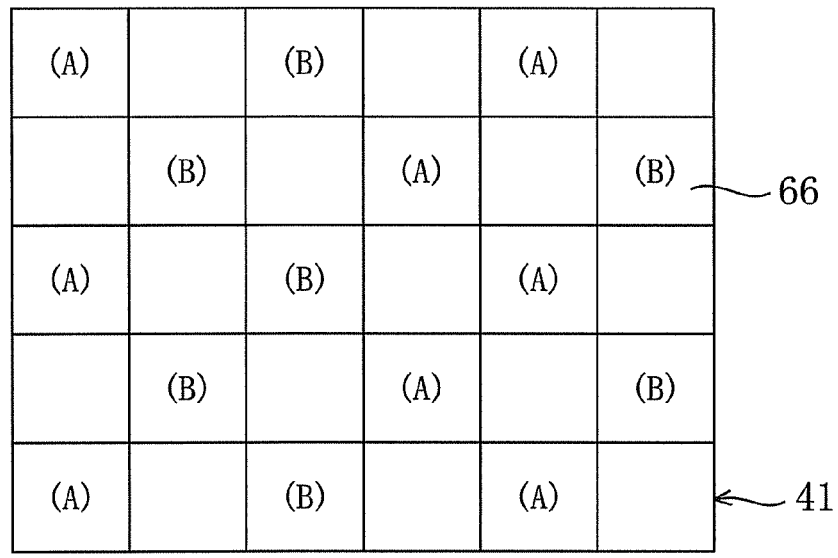
FIG. 18 is a schematic diagram representing another example of a pattern that may be formed on a plate.

For example, similarly to Example 1, a hydrophilic surface can be formed in a lattice pattern as illustrated in FIG. 15, a pattern of a plurality of concentric circles as illustrated in FIG. 16, a checkerboard pattern as illustrated in FIG. 17, or a checkerboard pattern as illustrated in FIG. 18; and fibroblasts can be cultured in areas 63, 65, and 66 of such patterns. Alternatively, epithelial cells, hepatocytes, osteoblasts or the like can be cultured similarly.

Although there are no particular limitations, the epithelial cells that can be used include, for example, corneal epithelial cells, oral mucous cells, amnion epithelial cells, keratinized cells, retinal pigment cells or the like; hepatocytes that can be used include, for example, liver parenchymal cells, endothelial cells, stellate cells, Kupffer cells or the like; osteoblasts that can be used include, for example, cells differentiated from stem cells such as mesenchymal stem cells or the like; and the medium that can be used to culture such cells includes, for example, D-MEM, MEM, RPMI1640, Medium199, F-10, F-12 or the like.

These "patterns composed of hydrophilic surfaces" as illustrated in FIGS. 15 to 18 are useful particularly when producing cell culture products of various different natures on a single plate. It is also useful for screening prescribed bioactive substances or analyzing the interactions between such substances and the cells.

Preferably, by applying lithography, a hydrophilic surface having a fine pattern surrounded by a water-repellent layer may be formed on a plate, and furthermore, a fine and compact cell culture region may be formed along the pattern. Therefore, a number of cell culture products with various forms can be produced on a single plate.

For example, in FIG. 17, the checkerboard pattern 66 is divided into portions (1), (2), (3) and (4), and desired four kinds of mutually different (for example various hepatocytes) cell culture products can be simultaneously obtained from a single plate. Alternatively, as illustrated in FIG. 18, the checkerboard pattern 66 is divided into portions (A) and (B), and two different kinds of osteoblasts can be simultaneously cultured on a single plate.

By using a substrate formed with such an orderly pattern as illustrated in the drawings and culturing common test cells in samples (of media) with varied nucleic acids (DNA or the like), proteins or the like predisposed in a prescribed pattern, it is possible to analyze interactions of each sample and the cells. Alternatively, for example, it can be used in screening for properties such as antimicrobial activity.

Further, the technology described herein provides a method for producing a block (mass) of embryonic stem cells (ES cells).

Figure 19:
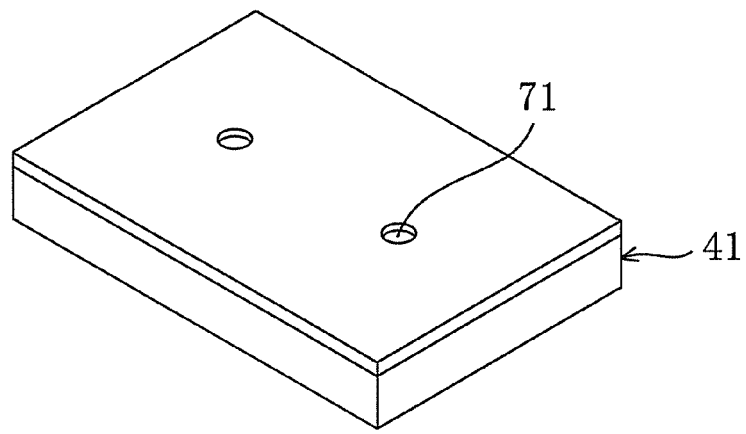
FIG. 19 is a schematic diagram representing another example of a pattern that may be formed on a plate.
Figure 20:
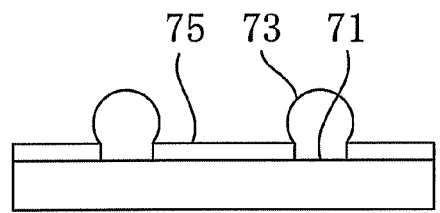
FIG. 20 is a schematic diagram representing a state in which culture medium has been disposed on a hydrophilic surface in an example.

For example, similarly as the above Example 1, a hydrophilic surface 71 is formed in a pattern of a plurality of dots with a diameter of approximately 1 mm as illustrated in FIG. 19. Embryonic stem cells are then inoculated to the patterned portion and cultured. In this case, as illustrated in FIG. 20, a medium 73 on the hydrophilic surface 71 strongly repels a water-repellent layer 75. Accordingly, a three-dimensional liquid droplet of near spherical shape can be formed. Therefore, an aggregate of the embryonic stem cells can be cultured in a three-dimensional shape (for example, near spherical shape with a diameter of approximately 1 mm to 5 mm) corresponding to the medium shape. Embryonic stem cells that can be used include mouse embryonic stem cells, crab-eating macaque embryonic stem cells, human embryonic stem cells or the like. The medium that can be used to culture such embryonic stem cells includes, for example, D-MEM, MEM, RPMI1640, Medium199, F-10, F-12 or the like.

Furthermore, the technology described herein is preferable for producing a cell culture product of a complex shape such as a tissue (organ) with a branching pattern.

Figure 21:
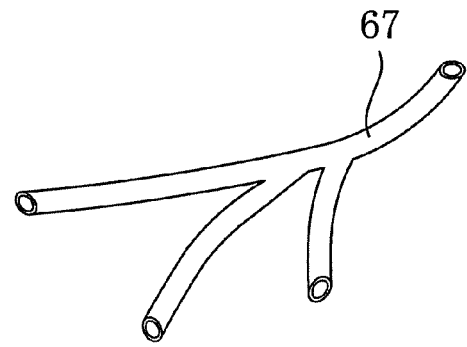
FIG. 21 is a schematic diagram representing a tubular cell culture product.

For example, similarly as the above Example 2, the hydrophilic surface 5 can be formed in a branching pattern as illustrated in FIG. 1(3), and vascular endothelium cells can be cultured in the branching pattern. Two pieces of such a vascular endothelium cell culture product in such a branching pattern are produced and placed in such a way that they may attach to each other. By culturing the attached product, can be obtained a tubular vascular endothelium cell culture product (therefore, blood vessel) 67 as illustrated in FIG. 21 because of the ability of the vascular endothelium cell groups to adhere to each other while leaving an inner cavity.

Figure 22:
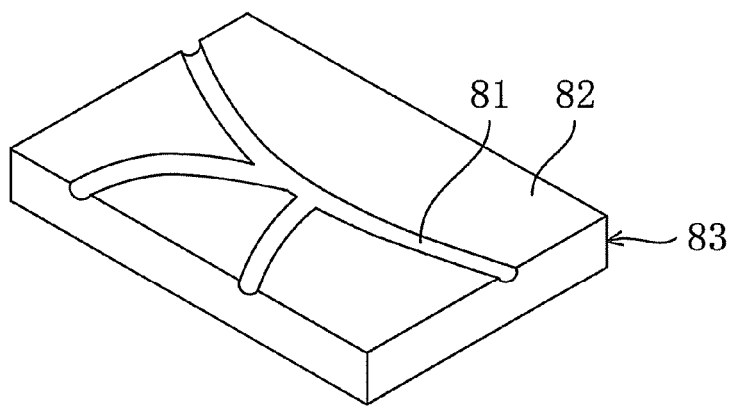
FIG. 22 is a schematic diagram representing an example of a plate, wherein a groove pattern composed of a hydrophilic surface is formed.
Figure 23:
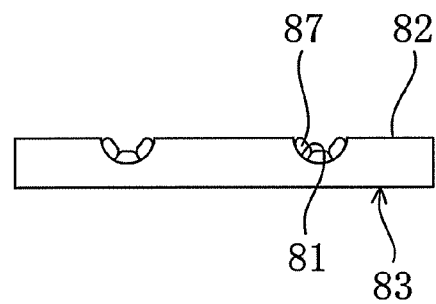
FIG. 23 is a schematic diagram representing a state in which cells have been deposited on the hydrophilic surface of the plate represented in FIG. 22.
Figure 24:
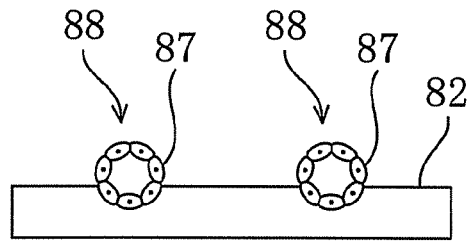
FIG. 24 is a schematic diagram representing a tubular cell culture product formed along (the groove pattern of) the hydrophilic surface on the plate represented in FIG. 22.

Alternatively, as illustrated in FIG. 22, by lithography, a groove 81 composed of a hydrophilic surface with a U-shaped cross-section can be formed in a prescribed pattern in a water-repellent layer 82 of a substrate 83. By inoculating and culturing prescribed vascular endothelium cells in the groove 81, can be produced a vascular endothelium cell culture product as a long string, which is one half of the tube split into two pieces along the longitudinal axis. For example, the radius of the near semi-circular shape cross-section of the groove 81 may be approximately 50 μm, and as illustrated in FIG. 23, a plurality (three are schematically illustrated in the drawing) of the above vascular endothelium cells (HUVEC) 87 can be deposited in the groove 81 and the cells can be cultured having a cross section in the extremely microscopic semi-circular shape. Accordingly, can be produced a partially-branched (branching), three-dimensional vascular endothelium cell culture product in a pattern with a U-shaped cross-section. When such product is further cultured, because of the characteristic ability of the endothelium cells 87 to adhere to each other in such a way to form an inner cavity, can be obtained a tubular vascular endothelium cell culture product 88 as illustrated in FIG. 24. As described above, such a tubular cell culture product may also be formed by attaching two cell culture products with a cross section of near semi-circular shape.

Figure 25:
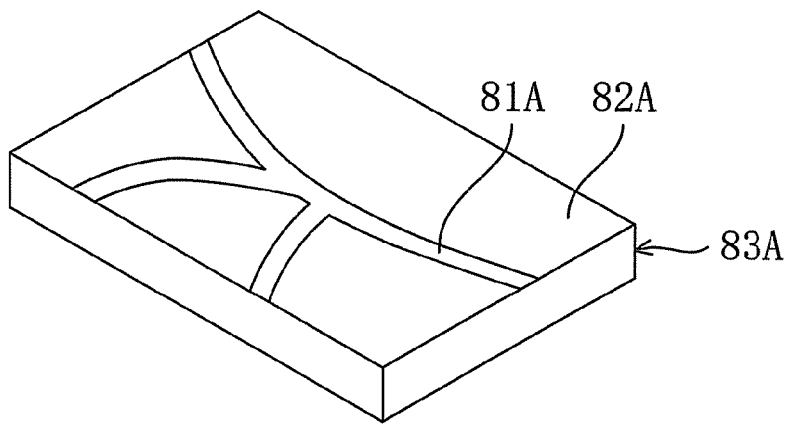
FIG. 25 is a schematic diagram representing an example of a plate with which a line pattern composed of the hydrophilic surface is formed.
Figure 26:
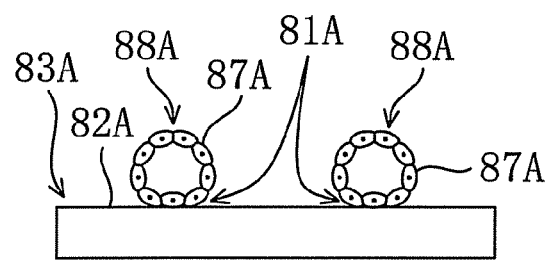
FIG. 26 is a schematic diagram representing a tubular cell culture product formed along (the linear pattern of) the hydrophilic surface of the plate represented in FIG. 25.

Such tubular vascular endothelium cell culture product 87 can be formed on a flat, linear hydrophilic surface instead of the above described grooved (U-shaped cross-section) hydrophilic surface. Specifically, as illustrated in FIG. 25, following the formation of an ultra water-repellent layer 82A (preferably, with a water droplet contact angle of 150° or greater) composed of a monomolecular layer on a substrate 83A, in a part thereof, can be formed a linear hydrophilic surface 81A in a prescribed pattern. For example, the width of the linear hydrophilic surface 81A may be approximately 50 μm. In this case, the medium that may be disposed only on the hydrophilic surface 81A will typically be protruding as droplets (for example, see FIG. 4) along the line of the hydrophilic surface 81A, and vascular endothelium cells 87A can be three-dimensionally cultured in the medium. Subsequently, these vascular endothelium cells 87A cultured in the medium disposed along the line of the hydrophilic surface 81A may attach to each other leaving a cavity inside to form a tubular vascular endothelium cell culture product 88A illustrated in FIG. 26.

Figure 27:
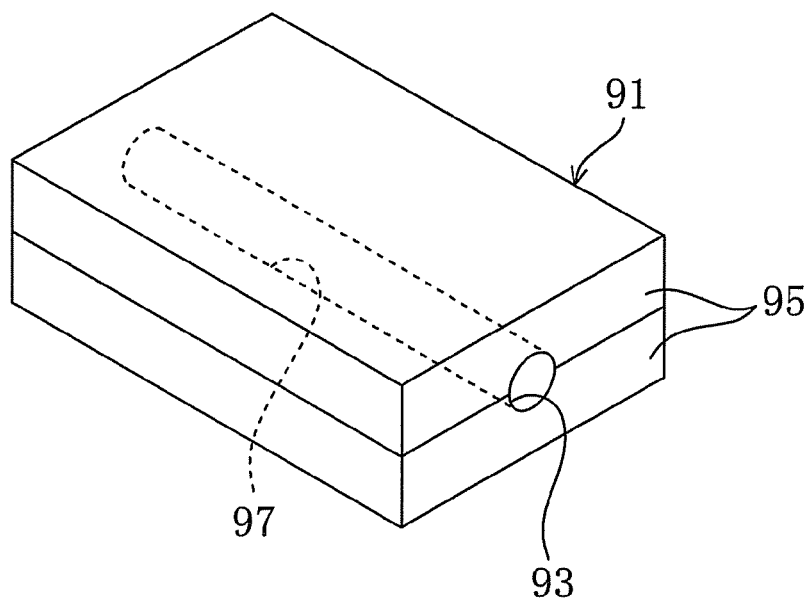
FIG. 27 is a schematic diagram representing an example of a plate, wherein a groove pattern composed of a hydrophilic surface is formed.
Figure 28:
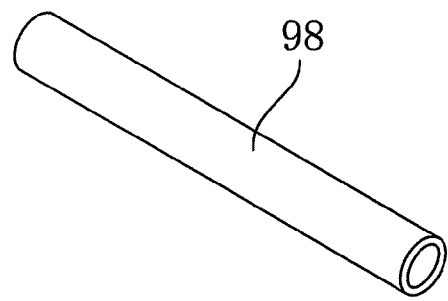
FIG. 28 is a schematic diagram representing a tubular cell culture product that may be obtained utilizing the plate of FIG. 27.

Alternatively, a plate 91 as illustrated in FIG. 27 may be prepared by attaching two plates 95 together, wherein grooves composed of a hydrophilic surface with a U-shaped cross-section as illustrated in FIG. 22 are formed in a prescribed pattern, respectively. A tubular vascular endothelium cell culture product 98 (see FIG. 28) can be readily formed by utilizing such a three-dimensional plate. In the attached plates 91, the hydrophilic surface is formed partially only on the surface of a fine through-hole 93 formed by the two facing fine grooves. Therefore, vascular endothelium cells can be selectively cultured on the surface of the through-hole 93 (in other words, the inner portion of the through-hole 93). The through-hole 93 may be filled with culture medium in advance and supplied with additional medium as needed. When inoculated on the inner wall 97 of the through-hole 93, because of the characteristic property of vascular endothelium cells to attach to each other to form a cavity in the inner portion, the cells will divide forming a tubular shape and as schematically illustrated in FIG. 28, can be obtained a tubular vascular endothelium cell culture product (vascular tissue) 98.

According to such embodiment, a tubular vascular endothelium cell culture product (vascular tissue) can be integrally and three-dimensionally formed (in other words, without a subsequent attachment). In addition, since the vascular tissue is formed along the through-hole 93 having good molding ability, its moldability (precision) is particularly excellent.

As described in the above examples, according to the present invention, a hydrophilic surface having a fine groove (or tubular) pattern surrounded by a water-repellent layer can be formed on a plate using a method such as lithography. Therefore, can be obtained a vascular endothelium cell culture product (vascular tissue) with a microscopic diameter (more preferably, also with complex branching) that has not been made available heretofore.

Example 3

<1> Manufacturing of Plate for Producing Tubular Cell Culture Product (i) Treatment of Substrate and Forming of Water-Repellent Layer:

A treatment similar to that in Example 1 was performed and a plate having a linear hydrophilic surface was prepared. Particularly, a 2 cm×2 cm-size plate made of silica glass was prepared as a substrate for cell culturing. A surface of the substrate was exposed for approximately 10 minutes to vacuum ultraviolet light (VUV) generated from the same excimer lamp as the one used in Example 1. In the present example, the spatial distance from the lamp to the substrate was approximately 10 mm. With the VUV irradiation, hydroxyl group (silanol group) was introduced to the surface of the substrate. Using the same materials and methods as in Example 1, was formed on the substrate surface a water-repellent layer (monomolecular layer) composed of a polysiloxane film with fluorine-substituted alkyl side chains as illustrated in FIG. 5. The static contact angle of distilled water (liquid droplet diameter of approximately 2 mm) on the surface of the water-repellent layer was measured under an atmosphere at 25° C. using the above described contact angle goniometer, and the water droplet contact angle was 150° or greater (typically, between 150° to 160°), illustrating extremely high water-repellency (ultra water-repellency).

(ii) Forming of Linear Hydrophilic Surface:

Was prepared a photomask (in this case, made of Cu) with a light-transmittable slit of approximately 20 μm in width and approximately 5 mm in length, which serves as the portion transmitting ultraviolet light. The substrate surface was irradiated through the photomask with excimer light having a wavelength of 172 nm. Accordingly, was obtained a plate for producing a tubular cell culture product (typically capillary vessels), wherein a linear hydrophilic surface of 20 μm to 30 μm in width and approximately 5 mm in length corresponding to the above slit was formed on the substrate surface.

<2> Production of Tubular Vascular Endothelium Cell Culture Product

A tubular cell culture product (capillary blood vessels) was produced using a plate prepared for this example as described above. As for the cells, the above-described HUVEC was used, and HuMedia-EG2 was used as the culture medium. In particular, the HUVEC subcultured in a prescribed dish in advance was treated with trypsin and suspended in a saline solution to prepare a cell suspension.

The above-described plate for producing a tubular cell culture product (typically capillary) was placed in a Petri dish with a diameter of 10 cm, and the cell suspension was added to the dish so that the number of cells was $1 \times 10^6$ and the total solution volume was 15 mL.

The Petri dish was placed into a $CO_2$ incubator and the cells were cultured at 37° C. in a 5% $CO_2$ atmosphere for seven days.

<3> Observation of Cell Culture Product

Figure 30:
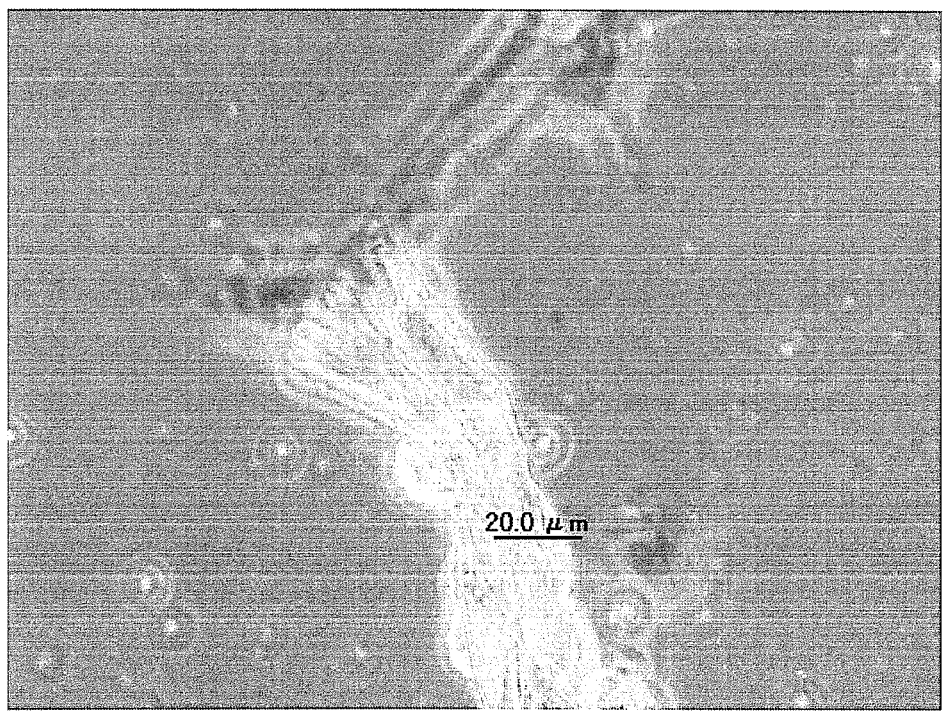
FIG. 30 is a microscope photo showing an enlarged terminal portion (A) of the tubular cell culture product shown in FIG. 29.
Figure 31:
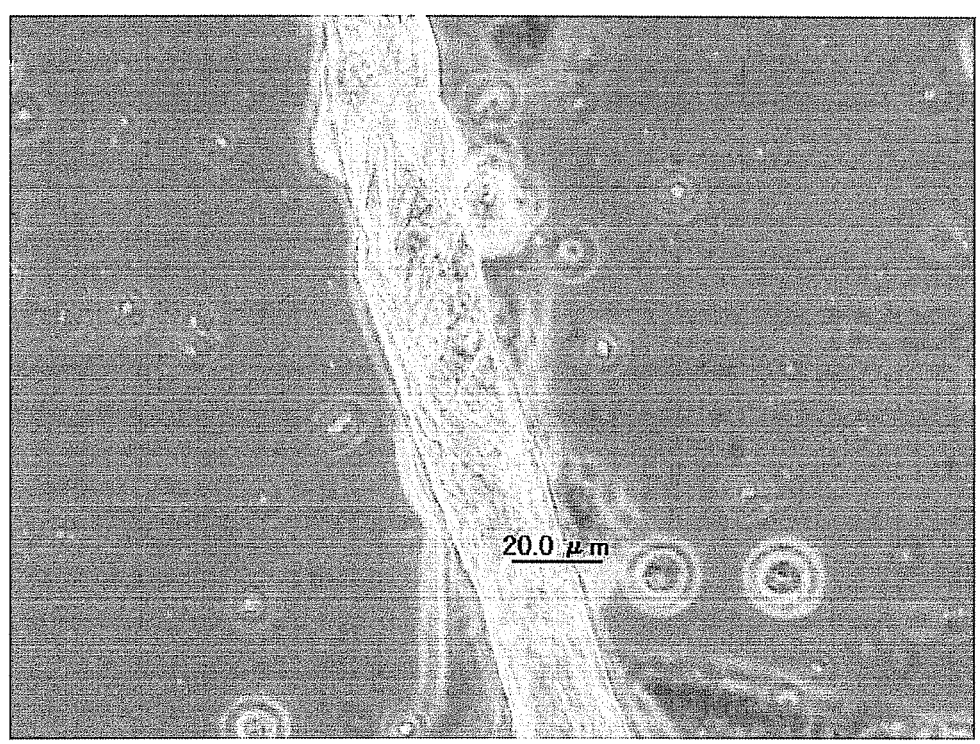
FIG. 31 is a microscope photo showing an enlarged mid portion (B) of the tubular cell culture product shown in FIG. 29.

The culture product at the seventh day of culturing was observed with a phase contrast microscope (model "IX70", available from OLYMPUS corporation). The microphotographs of the culture product are shown in FIGS. 29, 30 and 31.

Figure 29:
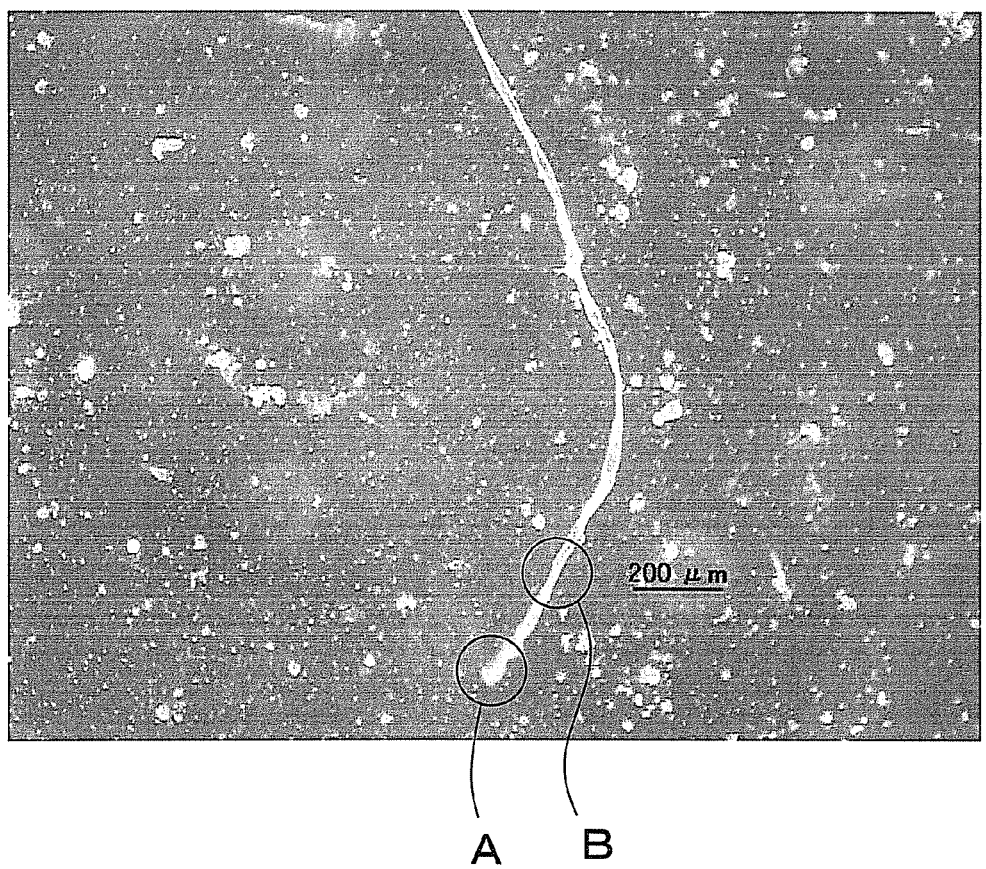
FIG. 29 is a phase-contrast microscope photo showing a part of a tubular cell culture product (a capillary vessel seven days after culture initiation) produced in an example.

As illustrated in FIG. 29 (the scale bar in the drawing is equivalent to 200 μm), the adherent cells (HUVEC) cultured on the plate in the present example did not adhere to the ultra water-repellent surface, but some of the cells adhered selectively to the linear hydrophilic surface. Moreover, a fine strand of tissue was formed as the cells attached to each other. Further, a cavity was observed in the central portion of the tissue strand as shown in FIGS. 30 and 31, which are magnified photographs of a terminal portion (A) and a mid portion (B), respectively, of the tissue strand shown in FIG. 29. Thus, the formation of a tubular tissue (capillary tissue) was observed.

Example 4

<1> Manufacturing of Plate for Producing Tubular Cell Culture Product

An 6-cm-diameter IWAKI™ Petri dish made of polystyrene (product of Asahi Techno Glass Corporation) was utilized as a substrate, and a treatment similar to that in Example 1 was performed to form an ultra water-repellent layer on the substrate surface. Thereafter, a plate (dish) having a linear hydrophilic surface was prepared by performing a treatment similar to that in Example 1.

<2> Production of Tubular Vascular Endothelium Cell Culture Product

A tubular vascular endothelium cell culture product was produced using a plate prepared for this example as described above. As for the cells, the above-described HUVEC was used, and HuMedia-EG2 was used as culture medium. In particular, the HUVEC subcultured in a prescribed dish in advance was treated with trypsin and suspended in a saline solution to prepare a cell suspension.

Thereafter, the cell suspension was added to the dish so that the number of cells was $4 \times 10^5$ and the total solution volume was 6 mL.

The Petri dish was then placed in a $CO_2$ incubator and the cells were cultured at approximately 37° C. in a 5% $CO_2$ atmosphere for seven days.

<3> Observation of Cell Culture Product

The culture product at the third day of culturing was observed with a phase contrast microscope (model "IX70", manufactured by OLYMPUS corporation). The microphotograph of the culture product is shown in FIG. 32.

Figure 32:
FIG. 32 is a phase-contrast microscope photo showing a part of a tubular cell culture product (three days after culture initiation) produced in an example.

As illustrated in FIG. 32 (the scale bar in the drawing is equivalent to 200 μm), the adherent cells (HUVEC) cultured on the plate in the present example did not adhere to the ultra water-repellent surface, but some of the cells adhered selectively to the linear hydrophilic surface. Moreover, a fine tubular tissue with a diameter of approximately 50 μm to 100 μm was observed as the cells attached to each other.

Example 5

<1> Manufacturing of Plate for Producing Tubular Cell Culture Product

A gelatin-coated substrate, prepared by coating the surface of an 6-cm-diameter IWAKI™ Petri dish made of polystyrene (product of Asahi Techno Glass Corporation) with gelatin was used.

A mask of 30 μm-diameter wire (not limited to any particular material) was disposed on the surface of the gelatin-coated substrate, and a treatment similar to that in Example 1 was performed to form an ultra water-repellent layer on the substrate surface. Subsequently, the mask was removed to obtain a plate (dish) having a linear gelatin-coated portion (here, a three-dimensional linear hydrophilic surface).

<2> Production of Tubular Vascular Endothelium Cell Culture Product

A tubular vascular endothelium cell culture product was produced using a plate prepared for the present example as described above. As for the cells, the above-described HUVEC was used, and HuMedia-EG2 was used as the culture medium. In particular, the HUVEC subcultured in a prescribed dish in advance was treated with trypsin and suspended in a saline solution to prepare a cell suspension.

Thereafter, the cell suspension was added to the dish so that the number of cells was $4 \times 10^5$ and the total solution volume was 6 mL.

The Petri dish was placed in a $CO_2$ incubator and the cells were cultured at approximately 37° C. in an approximately 5% $CO_2$ atmosphere for seven days. In addition, as a comparison, cell culturing was carried out similarly on a gelatin-coated substrate without the process to form a ultra water-repellent layer using a mask (in other words, on a dish, wherein the entire surface was coated with gelatin).

<3> Observation of Cell Culture Product

Figure 33:
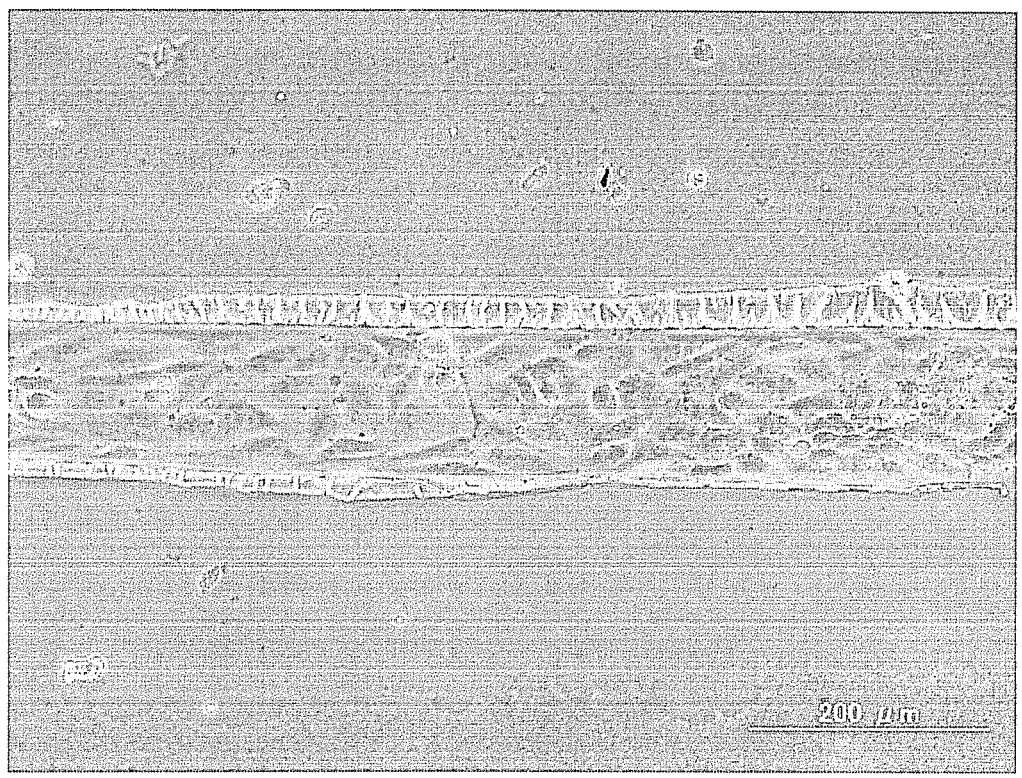
FIG. 33 is a phase-contrast microscope photo showing a part of a tubular cell culture product (three days after culture initiation) produced in an example.
Figure 34:
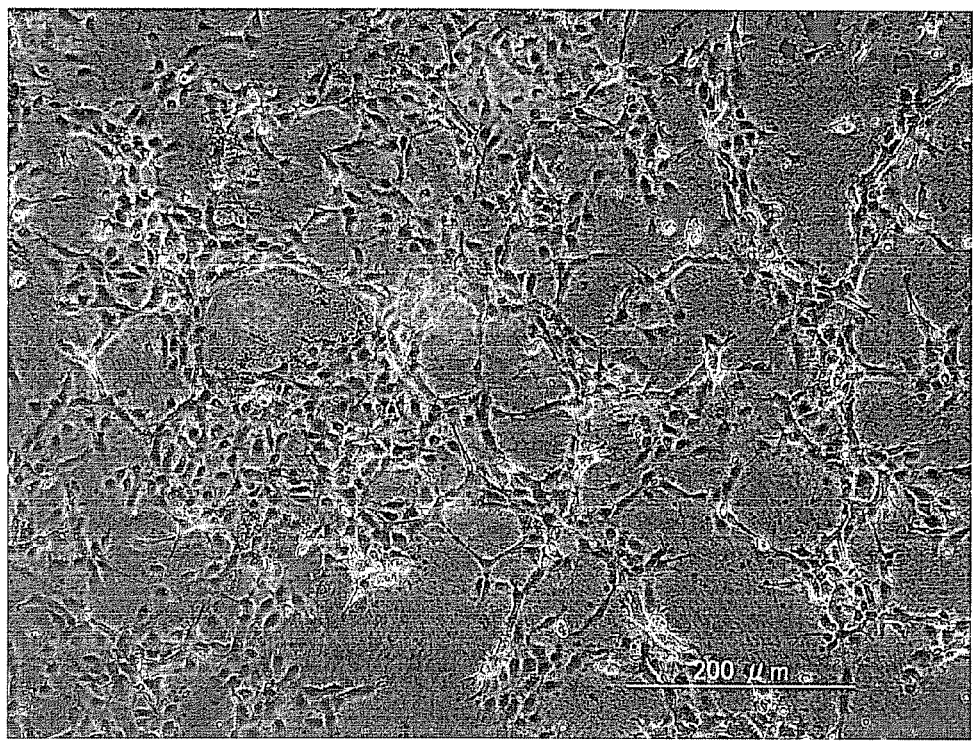
FIG. 34 is a phase-contrast microscope photo showing a part of a cell culture product (three days after culture initiation) adhered to a plate in a comparative example.

The culture product at the third day of culturing was observed with a phase contrast microscope (model "IX70", manufactured by OLYMPUS corporation). In FIG. 33 is shown a microphotograph of the culture product obtained by utilizing the plate for the present example. Shown in FIG. 34 is a microphotograph of the culture product obtained by utilizing the comparative plate.

As illustrated in FIG. 33 (the scale bar in the drawing is equivalent to 200 μm), the adherent cells (HUVEC) cultured on the plate in the present example did not adhere to the ultra water-repellent surface, but aggregated on the linear hydrophilic surface coated with gelatin, while some of the cells selectively adhered to the linear hydrophilic surface. Moreover, a fine tubular tissue with a diameter of approximately 100 μm to 200 μm was observed as the cells attached to each other. In contrast, as illustrated in FIG. 34 (the scale bar in the drawing is equivalent to 200 μm), in the case where the entire surface of the plate is hydrophilic, no cell aggregation or formation of a tubular tissue as shown in FIG. 33 was observed, and the cultured cells were adhered randomly to the plate surface.

Based on the results from each of the above Examples, it has been observed that by culturing/growing vascular endothelium cells such as HUVEC or the like on a substrate provided by the present invention, can be easily produced a tubular vascular endothelium cell culture product (thus, capillary vessels) of a desired size, preferably a diameter of approximately 200 μm or smaller (for example 20 μm to 30 μm).

In addition, although not specifically exemplified, by using a plate for cell culture product formation provided by the present invention, wherein a hydrophilic surface in a prescribed pattern (that is, a patterned cell culturing region) is formed, can be obtained, as an organized cell culture product on a plate, other tissue and organs of a complex and intricate structure, such as tubular tissue other than vascular tissue and the like.

Specific embodiments of the present invention were described in detail above. However, these are merely illustrative and are not to limit the scope of the claims. The technology described in the claims also includes various changes and modifications of the specific examples illustrated above.

What is claimed is:

1. A method for producing a cell culture product in a desired pattern, the method comprising:
    preparing a plate for cell culture, the plate having a hydrophilic surface formed in a groove of a width of less than or equal to 100 μm and a water repellent surface having a water contact angle of greater than 150° formed in areas other than the groove;
    disposing protruding droplets of a culture medium selectively along the groove on the hydrophilic surface; and
    culturing a target cell in the disposed medium.

2. The method of claim 1, wherein the water repellent surface is formed of a high molecular weight organic compound having an alkyl, alkenyl, or alkynyl group substituted or not substituted with a functional group capable of bonding to the plate.

3. The method of claim 2, wherein the high molecular weight organic compound is an organic compound having a functional group capable of bonding to the plate and an alkyl, alkenyl or alkynyl group substituted entirely or partially with fluorine.

4. The method of claim 1, wherein the water repellent surface is formed of a monomolecular layer.

5. The method of claim 1, wherein the water repellent surface is formed of a polysiloxane film with fluorine substituted alkyl side chains.

6. The method of claim 1, wherein the groove is formed by removing a portion of the water repellent layer from the plate by lithography.

7. The method of claim 1, wherein the cell is an embryonic stem cell or a bone marrow stem cell.

8. A method for producing a cell culture product in a desired pattern, the method comprising:
preparing a plate for cell culture, the plate having a hydrophilic surface formed in a groove of a width of less than or equal to 100 μm and a water repellent surface having a water contact angle of greater than 150° formed in areas other than the groove; and
culturing a target adherent cell in a state in which the cells are adhered selectively to the hydrophilic surface, wherein protruding droplets of a culture medium are disposed along the groove of the hydrophilic surface.

9. The method of claim 8, wherein the water repellent surface is formed of a high molecular weight organic compound having an alkyl, alkenyl, or alkynyl group substituted or not substituted with a functional group capable of bonding to the plate.

10. The method of claim 9, wherein the high molecular weight organic compound is an organic compound having a functional group capable of bonding to the plate and an alkyl, alkenyl or alkynyl group substituted entirely or partially with fluorine.

11. The method of claim 8, wherein the water repellent surface is formed of a monomolecular layer.

12. The method of claim 8, wherein the water repellent surface is formed of a polysiloxane film with fluorine substituted alkyl side chains.

13. The method of claim 8, wherein the groove is formed by removing a portion of the water repellent layer from the plate by lithography.

14. The method of claim 8, wherein the adherent cell is one selected from the group consisting of a vascular endothelium cell, a neural cell, a fibroblast, a hepatocyte, and an osteoblast.

15. The method of claim 8, wherein the cell culture product is a capillary network.

* * * * *